United States Patent
Liu et al.

(10) Patent No.: US 8,716,422 B2
(45) Date of Patent: *May 6, 2014

(54) ANIONIC CHARGE-DYNAMIC POLYMERS FOR RELEASE OF CATIONIC AGENTS

(71) Applicant: Wisconsin Alumni Research Foundation, Madison, WI (US)

(72) Inventors: Xianghui Liu, Metairie, LA (US); Jingtao Zhang, Lansdale, PA (US); David M. Lynn, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/658,446

(22) Filed: Oct. 23, 2012

(65) Prior Publication Data

US 2013/0122055 A1 May 16, 2013

Related U.S. Application Data

(62) Division of application No. 12/479,582, filed on Jun. 5, 2009, now Pat. No. 8,324,333.

(60) Provisional application No. 61/059,194, filed on Jun. 5, 2008.

(51) Int. Cl.
*C08F 20/58* (2006.01)
*A61K 47/30* (2006.01)

(52) U.S. Cl.
USPC ........................................ 526/304; 514/772.4

(58) Field of Classification Search
None
See application file for complete search history.

(56) References Cited

U.S. PATENT DOCUMENTS

| | | |
|---|---|---|
| 5,266,446 A | 11/1993 | Chang et al. |
| 5,948,878 A | 9/1999 | Burgess et al. |
| 6,217,912 B1 | 4/2001 | Park et al. |
| 6,274,322 B1 | 8/2001 | Curiel et al. |
| 6,312,727 B1 | 11/2001 | Schacht et al. |
| 6,353,055 B1 | 3/2002 | Kabanov et al. |
| 6,365,173 B1 | 4/2002 | Domb et al. |
| 6,383,811 B2 | 5/2002 | Wolff et al. |
| 6,395,253 B2 | 5/2002 | Levy et al. |

(Continued)

FOREIGN PATENT DOCUMENTS

| | | |
|---|---|---|
| WO | WO 2003/035716 | 5/2003 |
| WO | WO 2004/009665 | 1/2004 |

(Continued)

OTHER PUBLICATIONS

Ai et al. (Feb. 2003) "Biomedical Applications of Electrostatic Layer-by-Layer Nano-assembly of Polymers, Enzymes, and Nanoparticles," Cell Biochem. Biophys. 39(1):23-43.

(Continued)

*Primary Examiner* — Brian Gulledge
(74) *Attorney, Agent, or Firm* — Lathrop & Gage LLP

(57) ABSTRACT

Materials and Methods for the generation of polyelectrolyte multilayers that can erode to release cationic components. The multilayers comprise layers that contain one or more cations and one or more charge-dynamic anionic polymers. Charge-dynamic anionic polymers contain side chains having removable functional groups. Removal of the functional groups results in a change in the net change in the charge of the polymer which can disrupt interactions between cations and the anionic polymers and facilitate release of cations.

21 Claims, 4 Drawing Sheets

(56) References Cited

U.S. PATENT DOCUMENTS

| | | | |
|---|---|---|---|
| 6,544,790 B1 | 4/2003 | Sabatini | |
| 6,586,524 B2 | 7/2003 | Sagara | |
| 6,652,886 B2 | 11/2003 | Ahn et al. | |
| 6,740,643 B2 | 5/2004 | Wolff et al. | |
| 6,743,521 B2 | 6/2004 | Hubbell et al. | |
| 6,770,740 B1 | 8/2004 | Rice et al. | |
| 6,998,115 B2 | 2/2006 | Langer et al. | |
| 7,112,361 B2 | 9/2006 | Lynn et al. | |
| 7,208,314 B2* | 4/2007 | Monahan et al. | 435/320.1 |
| 7,427,394 B2 | 9/2008 | Langer et al. | |
| 8,324,333 B2 | 12/2012 | Liu et al. | |
| 2001/0006817 A1 | 7/2001 | Pack et al. | |
| 2002/0012652 A1 | 1/2002 | Levy et al. | |
| 2002/0131951 A1 | 9/2002 | Langer et al. | |
| 2002/0146459 A1 | 10/2002 | Levy et al. | |
| 2002/0164315 A1 | 11/2002 | Wolf et al. | |
| 2003/0026840 A1 | 2/2003 | Plank et al. | |
| 2003/0073619 A1 | 4/2003 | Mahato et al. | |
| 2005/0027064 A1 | 2/2005 | Lynn et al. | |
| 2005/0265956 A1 | 12/2005 | Liu et al. | |
| 2005/0282925 A1 | 12/2005 | Schlenoff et al. | |
| 2006/0051396 A1 | 3/2006 | Hamilton et al. | |
| 2006/0093607 A1 | 5/2006 | Gerber et al. | |
| 2006/0251701 A1 | 11/2006 | Lynn et al. | |
| 2007/0020469 A1 | 1/2007 | Wood et al. | |
| 2008/0286345 A1 | 11/2008 | Lynn et al. | |
| 2009/0170179 A1 | 7/2009 | Lynn et al. | |

FOREIGN PATENT DOCUMENTS

| | | |
|---|---|---|
| WO | WO 2004/009666 | 1/2004 |
| WO | WO 2004/106411 | 12/2004 |
| WO | WO 2005/007819 | 1/2005 |
| WO | WO 2007/140391 | 12/2007 |
| WO | WO 2007/140402 | 12/2007 |
| WO | WO 2009/049092 | 4/2009 |

OTHER PUBLICATIONS

Akinc et al. (2003) "Parallel Synthesis and Biophysical Characterization of a Degradable Polymer Library for Gene Delivery," J. Am. Chem. Soc. 125(18):5316-5323.
Aldersley et al. (1974) "Intramolecular Catalysis of Amide Hydrolysis by the Carboxy-Group. Rate Determining Proton Transfer from External General Acids in the Hydrolysis of Substituted Maleamic acids," J. Chem. Soc. Perk. Trans. 2 :1487-1495.
Anderson et al. (Apr. 30, 1998) "Human Gene Therapy," Nature 392(Supp):25-30.
Bae, Y. et al. (2003) "Design of Environment-Sensitive Supramolecular Assemblies for Intracellular Drug Delivery: Polymeric Micelles that are Responsive to Intracellular pH Change," Angew. Chem. Int. Ed. 42:4640-4643.
Barrera et al. (1993) "Synthesis and RGD Peptide Modification of New Biodegradable Copolymer: Poly(Lactic Acid-co-lysine)," J. Am. Chem. Soc. 115(23):11010-11011.
Benns et al. (2000) "pH-Sensitive Cationic Polymer Gene Delivery Vehicle: N-Ac-poly(L-histidine)-graft-poly(L-lysine) Comb Shaped Polymer," Bioconjugate Chem. 11:637-645.
Berg et al. (2006) "Controlled Drug Release from Porous Polyelectrolyte Multilayers," Biomacromolecules 7:357-364.
Bertrand et al. (Apr. 2000) "Ultrathin Polymer Coatings by Complexation of Polyelectrolytes at Interfaces: Suitable Materials, Structure and Properties," Macromol. Rapid Comm. 21(7):319-348.
Bindels et al. (1985) "The Reaction of Citrconic Anhydride with Bovine alpha-Crystallin Lysine Residues. Surface Probing and Dissociation-reassociation Studies," Biochem. Biophys. Acta 828:255-260.
Blacklock et al. (Jan. 2007) "Disassembly of Layer-by-Layer Films of Plasmid DNA and Reducible TAT Polypeptide," Biomaterials 28(1):117-124.
Boulmedais et al. (2003) "Buildup of Exponentially Growing Multilayer Polypeptide Films with Internal Secondary Structure," Langmuir 19(2):440-445.

Boussif et al. (Aug. 1995) "A Versatile Vector for Gene and Oligonucleotide Transfer into Cells in Culture and In Vivo: Polyethylenimine," Proc. Nat. Acad. Sci. USA 92:7297-9301.
Bronich, T.K. et al (2000) Recognition of DNA Topology in Reactions between Plasmid DNA and Cationic Copolymers, J. Am. Chem. Soc. 122(35) pp. 8339-8343.
Buck et al. (2007) "Layer-by-Layer Assembly of Reactive Ultrathin Films Mediated by Click-Type Reactions of Poly(2-Alkenyl Azlactone)s," Adv. Mater. 19(22):3951-3955.
Chan et al. (1997) "Triplex DNA: Fundamentals, Advances, and Potential Applications for Gene Therapy," J. Mol. Med. 75:267-282.
Chen et al. (2001) "Fabrication of a Covalently Attached Multilayer Film via In-Situ Reaction," Macromol. Rapid Commun. 22:311-314.
Chen et al. (Apr. 2007) "Tunable Film Degradation and Sustained Release of Plasmid DNA from Cleavable Plycation/Plasmid DNA Multilayers under Reductive Conditions," Small 3(4):636-643.
Cho et al. (2003) "Polymeric Multilayer Films Comprising Deconstructable Hydrogen-Bonded Stacks Confined Between Electrostatically Assembled Layers," Macromolecules 36(8):2845-2851.
Cotton et al. (1993) "[42] Receptor-Mediated Transport of DNA into Eukaryotic Cells," Methods Enzymol. 217:618-644.
Crystal, R.G. (Oct. 20, 1995) "Transfer of Genes to Humans: Early Lessons and Obstacles to Success," Science 270(5235):404-410.
De Geest et al. (2007) "Release Mechanisms for Polyelectrolyte Capsules," Chem. Soc. Rev. 36:636-649.
De Geest et al. (Apr. 2006) "Intracellularly Degradable Polyelectrolyte Microcapsules," Adv. Mater. 18(8):1005-1009.
Decher, G. (Aug. 1997) "Fuzzy Nanoassemblies: Toward Layered Polymeric Multicomposites," Science 277:1232-1237.
Dixon et al. (1968) "Reversible Blocking of Amino Groups with Citraconic Anhydride," Biochem J. 109:312-314.
Donbrow, M. (1992) "Developments in Phase Separation Methods, Aggregation Control, and Mechanisms of Microencapsulation," In; Microcapsules and Nanoparticles in Medicine and Pharmacy, CRC Press, Boca Raton pp. 17-45.
Dubas et al. (2001) "Multiple Membranes from "True" Polyelectrolyte Multilayers," J. Am. Chem. Soc. 123(22):5368-5369.
Dubas et al. (2001) "Polyelectrolyte Multilayers Containing a Weak Polyacid: Construction and Deconstruction," Macromolecules 34(11):3736-3740.
Etienne et al. (2005) "Degradability of Polysaccharides Multilayer Films in the Oral Environment: An In Vitro and In Vivo Study," Biomacromolecules 6(2):726-733.
Feng et al. (2005) "Reactive Thin Films as Platforms for the Immobilization of Biomolecules," Biomacromolecules 6(6):3243-3251.
Feng et al. (Jul. 2006) "Fabrication of Robust Biomolecular Patters by Reactive Microcontact Printing on N-Hydroxysuccinimide Ester-Containing Polymer Films," Adv. Funct. Mater. 16(10):1306-1312.
Fishbein et al. (2005) "Site Specific Gene Delivery in the Cardiovascular System," J. Control. Release 109:37-48.
Fishbein et al. (2006) "Bisphosphonate-Mediated Gene Vector Delivery from the Mental Surfaces of Stents," Proc. Natl. Acad. Sci. USA 103:159-164.
Forrest et al. (Feb. 2004) "Partial Acetylation of Polyethylenimine Enhances In Vitro Gene Delivery," Pharm. Res. 21(2):365-371.
Fredin et al. (2005) "Surface Analysis of Erosion Multilayered Polyelectrolyte Films: Nanometer-Scale Structure and Erosion Profiles," Langmuir 21:5803-5811.
Fredin et al. (2007) "Nanometer-Scale Decomposition of Ultrathin Multilayered Polyelectrolyte Films," Langmuir 23:2273-2276.
Funhoff et al. (Jan. 2004) "Polymer Side-Chain Degradation as a Tool to Control the Destabilization of Polyplexes," Pharm. Res. 21(1):170-176.
Godbey et al. (1999) "Size Matters: Molecular Weight Affects the Efficient of Poly(ethylenimine) as a Gene Delivery Vehicle," J. Biomed. Mater. Res.45:268-275.
Godbey et al. (Apr. 1999) "Tracking the Intracellular Path of Poly(ethylenimine)/DNA Complexes for Gene Delivery," Proc. Nat. Acad. Sci. USA 96:5177-5181.
Goeddel (1990) "[1] Systems for Hetertologous Gene Expression," Methods Enzymol. 185:3-7.
Gonzalez et al. (1999) "New Class of Polymers for the Delivery of Macromolecular Therapeutics," Bioconjugate Chem. 10:1068-1074.

(56) References Cited

OTHER PUBLICATIONS

Gosselin et al. (2001) "Efficient Gene Transfer Using Reversibly Cross-Linked Low Molecular Weight Poluethylenimine," Bioconjugate Chem. 12:989-994.
Grayson et al. (2003) "Multi-Pulse Drug Delivery from a Resorbable Polymeric Microchip Device," Nat. Mater. 2:767-772.
Groth et al. (2004) "Layer-by-Layer Deposition of Polyelectrolytes—A Versatile Tool for the In Vivo Repair of Blood Vessels," Angew Chem. Int. Ed. Engl. 43:926-928.
Hammond, P.T. (2004) "Form and Function in Multilayer Assembly: New Applications at the Nanoscale," Adv. Mater. 16:1271-.
Heilmann et al. (Nov. 1, 2001) "Chemistry and Technology of 2-Alkenyl Azlactones," J. Polym. Sci. A Polym. Chem. 39(21):3655-3677.
Hiller et al. (2002) "Reversibly Erasable Nanoporous Anti-Reflection Coatings from Polyelectrolyte Multilayers," Nat. Mater. 1:59-63.
Jeong et al. (2001) "DNA Transfection Using Linear Poly(ethylenimine) Prepared by Controlled Acid Hydrolysis of Poly(2-ethyl-2-oxazoline)," J. Control. Release 73:391-399.
Jessel et al. (Jun. 6, 2006) "Multiple and Time-Schedules In Situ DNA Delivery Mediated by β-Cyclodextrin Embedded in a Polyelectrolyte Multilayer," Proc Nat. Acad. Sci. USA 103(23):8618-8621.
Jewell et al. (2005) "Multilayered Polyelectrolyte Films Promote the Direct and Localized Delivery of DNA to Cells," J. Control. Release 106:214-223.
Jewell et al. (2006) Release of Plasmin DNA from Intravascular Stents Coated with Ultrathin Multilayered Poly Biomacromolecules 7:2483-2491.
Jewell et al. (2008) "Multilayered Polyelectrolyte Assemblies as Platforms for the Delivery of DNA and Other Nucleic Acid-Based Therapeutics," Adv. Drug Deliv. Rev. 60:979-999.
Jewell et al. (2008) "Surface-Mediated Delivery of DNA: Cationic Polymers Take Charge," Curr. Opin. Colloid Interface Sci. 13:395-402.
Jiang et al. (2007) "Degradable-Brushed pHEMA-pDMAEMA Synthesized ATRP and Click Chemistry for Gene Delivery," Bioconjugate Chem. 18(6):2077-2084.
Kirby et al. (1972) "Structure and Efficiency in Intramolecular and Enzymatic Catalysis. Catalysis of Amide Hydrolysis by the Carboxy-Group of Substituted Maleamic Acids," J. Chem. Soc. Perk. Trans. 2 9:1206-1214.
Kircheis et al. (2001) "Design and Gene Delivery Activity of Modified Polyethylenimines," Adv. Drug Delivery Rev. 53:341-358.
Klugherz et al. (2000) "Gene Delivery from a DNA Controlled-Release Stent in Porcine Coronary Arteries," Nat. Biotechnol. 18:1181-1184.
Kwon et al. (1989) "Pseudopoly(amino Acids): A Study of the Synthesis and Characterization of poly(trans-4-hydroxy-N-acyl-L-proline esters)," Macromolecules 22(8):3250-3255.
Lahann et al. (2002) Reactive Polymer Coatings: A Platform for Patterning Proteins and Mammalian Cells onto a Broad Range of Materials, Langmuir 18(9):3632-3638.
Lahann et al. (2003) "Reactive Polymer Coatings: A First Step Toward Surface Engineering of Microfluidic Devices," Anal. Chem. 75:2117-2122.
Lavalle et al. (2004) "Direct Evidence for Vertical Diffusion and Exchange Processes of Polyanions and Polycations in Polyelectrolyte Multilayer Films," Macromolecules 37(3):1159-1162.
Lee et al. (2007) "A Protein Nanocarrier from Charge-Conversion Polymer in Response to Endosomal pH," J. Am. Chem. Soc. 129(17):5362-5363.
Lee, Y. et al. (2009) Charge Conversional Polyionic Complex Micelles-Efficient Nanocarriers for Protein Delivery into Cytoplasm, Anglewande Chemie Int'l Ed., 28, 5309-5312.
Li et al. (2004) "Multilayer Biomimetics: Reversible Covalent Stabilization of a Nanostructured Biofilm," Biomacromolecules 5(5):1667-1670.
Liang et al. (2004) "Multilayer Assembly and Patterning of Poly(p-phenylenecinylene)s via Covalent Coupling Reactions," Langmuir 20(22):9600-9606.
Liang et al. (2006) "Covalent Layer-by-Layer Assembly of Conjugated Polymers and CdSe Nanoparticles: Multilayer Structure and Photovoltaic Properties," Funct. Mater. 16:542-548.
Lim et al. (1999) "A Self-Destroying Polycationic Polymer: Biodegradable Poly(4-hydroxy-L-proline Ester)," J. Am. Chem. Soc. 121(24):5633-5639.
Lim et al. (2000) "Development of a Safe Gene Delivery System Using Biodegradable Polymer, Poly[alpha-(4-aminobutyl)-L-glycolic Acid]," J. Am. Chem. Soc. 122:6524-6525.
Little et al. (2004) "Poly-Beta Amino Ester-Containing Microparticles Enhance the Activity of Nonviral Genetic Vaccines," Proc. Nat. Acad. Sci. USA 101:9534-9539.
Liu et al. (2005) "Charge-Shifting Cationic Polymers that Promote Self-Assembly and Self-Disassembly with DNA," Macromolecules 38:7907-7914.
Liu et al. (2008) "Polyelectrolyte Multilayers Fabricated from 'Charge-Shifting' Anionic Polymers: A New Approach to Controlled Film Disruption and the Release of Cationic Agents from Surfaces," Soft Matter 4:1688-1695.
Lu et al. (Feb. 2008) "Biodegradable Polycation and Plasmid ZDNA Multilayer Film for Prolonged Gene Delivery to Mouse Osteoblasts," Biomaterials 29(6):733-741.
Luo et al. (2000) "Synthetic DNA Delivery Systems," Nat. Biotechnol. 18:33-37.
Luten et al. (2006) "Methacrylamide Polymers with Hydrolysis-Sensitive Cationic Side Groups as Degradable Gene Carriers," Bioconjugate Chem. 17(4):1077-1084.
Lvov et al. (1994) "Assembly of Thin Films by Means of Successive Deposition of Alrenate Layers of DNA and Poly(allylamine)," Macromolecules 26(20):5396-5399.
Lynn et al. (2000) "Degradable Poly(beta-amino Esters): Synthesis Characterization, and Self-Assembly with Plasmid DNA," J. Am. Chem. Soc. 122:10761-10768.
Lynn et al. (2001) "Accelerated Discovery of Synthetic Transfection Vectors: Parallel Synthesis and Screening of a Degradable Polymer Library," J. Am. Chem. Soc. 123:8155-8156.
Lynn, D.M. (2006) "Layers of Opportunity: Nanostructured Polymer Assemblies for the Delivery of Macromolecular Therapeutics," Soft Matter. 2:269-273.
Lynn, D.M. (2007) "Peeling Back the Layers: Controlled Erosion and Triggered Disassembly of Multilayered Polyelectrolyte Thin Films," Adv. Mater. 19:4118-4130.
Mathiowitz et al. (1987) "Novel Microcapsules for Delivery Systems," Reactive Polymers 6:275-283.
Mathiowitz et al. (1987) "Polyanhydride Microspheres as Drug Carriers. I. Hot-Melt Microencapsulation," J. Controlled Release 5:13-22.
Mathiowitz et al. (1988) "Polyanhydride Microspheres as Drug Carriers. II. Microencapsulation by Solvent Removal," J. Appl. Polymer Sci. 35:755-774.
Mendelsohn et al. (2006) "Fabrication of Microporous Thin Films from Polyelectrolyte Multilayers," Langmuir 16(11):5017-5023.
Meyer et al. (Sep. 2007) "A dimethylmaleic Acid-Melittin-polylysine Conjugate with Reduced Toxicity, pH-Triggered Endosomolytic Activity and Enhanced Gene Transfer Potential," J. Gene Med. 9(9):797-805.
Midoux et al. (1999) "Efficient Gene Transfer by Histidylated Polylysine/pDNA Complexes," Bioconjugate Chem. 10:406-411.
Nolte et al. (2004) "Creating Effective Refractive Index Gradients Within Polyelectrolyte Multilayer Films: Molecularly Assembled Rugate Filters," Langmuir 20(8):3304-3310.
Oupicky et al. (2002) "Laterally Stabilized Complexes of DNA with Linear Reducible Polycations: Strategy for Triggered Intracellular Activation of DNA Delivery Vectors," J. Am. Chem. Soc. 124(1):8-9.
Pack et al. (2005) "Design and Development of Polymers for Gene Delivery," Nat. Rev. Drug Disc. 4:581-593.
Perlstein et al. (2003) "DNA Delivery from an Intravascular Stent with a Denatures Collagen-Polylactic-Polyglycolic Acid-Controlled Release Coating: Mechanisms of Enhanced Transfection," Gene Ther. 10:1420-1428.

(56) References Cited

OTHER PUBLICATIONS

Peterson et al. (2002) "Poly(ethyleneimine-co-L-lactamide-co-succinamide): A Biodegradable Polyethyleneimine Derivative with an Advantageous pH-Dependent Hydrolytic Degradation for Gene Delivery," Bioconjugate Chem. 13:812-821.
Peyratout et al. (Jul. 19, 2004) "Tailor-Made Polyelectrolyte Microcapsules: From Multilayers to Smart Containers," Angew. Chem. Int. Ed. 43(29):3762-3783.
Picart et al. (Nov. 2005) "Controlled Degradability of PolySaccharide Multilayer Films In Vitro and In Vivo," Adv. Funct. Mater. 15(11):1771-1780.
Picart et al. (Oct. 1, 2002) "Molecular Basis for the Explanation of the Exponential Growth of Polyelectrolyte Multilayers," Proc. Nat. Acad. Sci. USA 99(20):12531-12535.
Pichon et al. (2002) "Poly[Lys-(AEDTP)]: A Cationic Polymer that Allows Dissociation of pDNA/Cationic Polymer Complexes in a Reductive Medium and Enhances Polyfection," Bioconjugate Chem. 13:76-82.
Prata et al. (2004) "Charge-Reversal Amphiphiles for Gene Delivery," J. Am. Chem. Soc. 126(39):12196-12197.
Putnam et al. (1999) "Poly(4-hydroxy-1-proline Ester): Low-Temperature Polycondensation and Plasmid DNA Complexation," Macromolecules 32:3658-3662.
Putnam et al. (Jan. 30, 2001) "Polymer-Based Gene Delivery with Low Cytotoxicity by a Unique Balance of Side-Chain Termini," Proc. Nat. Acad. Sci USA 98(3):1200-1205.
Rebuffat, A. et al. (2001) "Selective Enhancement of Gene Transfer by Steroid-Mediated Gene Delivery," Nature Biotechnology 19 pp. 1155-1161.
Ren et al. (2006) "Tunable DNA Release from Cross-Linked Ultrathin DNA/PLL Multilayered Films," Bioconjugate Chem. 17(1):77-83.
Ren et al. (Mar. 2006) "Construction and Enzymatic Degradation of Multilayered Poly-l-lysine/DNA Films," Biomaterials 27(7):1152-1159.
Richardson et al. (2001) "Polymeric System for Dual Growth Factor Delivery," Nat. Biotechnol. 19:1029-1034.
Richert et al. (2004) "Improvement of Stability and Cell Adhesion Properties of Polyelectrolyte Multilayer Films by Chemical Cross-Linking," Biomacromolecules 5(2):284-294.
Richert et al. (2004) "Layer by Layer Buildup of Polysaccharide Films: Physical Chemistry and Cellular Adhesion Aspects," Langmuir 20(2):448-458.
Rozema et al. (2003) "Endosomolysis by Masking of a Membrane-Active Agent (EMMA) for Cytoplasmic Release of Macromolecules," Bioconjugate Chem. 14(1):51-57.
Rozema et al. (Aug. 7, 2007) "Dynamic PolyConjugates for Targeted in Vivo Delivery of siRNA to Hepatocytes," Proc. Nat. Acad. Sci. USA 104(32):12982-12987.
Saltzman et al. (Mar. 2002) "Building Drug Delivery into Tissue Engineering Design," Nat. Rev. Drug Discov. 1(3):177-186.
Santini et al. (Jan. 29, 1999) "A Controlled-Release Microchip," Nature 397:335-338.
Saul et al. (Nov. 2007) "Delivery of Non-Viral Gene Carriers from Sphere-Templated Fibrin Scaffolds for Sustained Transgene Expression," Biomaterials 28(31):4705-4716.
Schaffer et al. (2000) "Vector Unpacking as a Potential Barrier for Receptor-Mediated Polyplex Gene Delivery," Biotechnol. Bioeng. 67(5):598-606.
Schneider et al. (2006) "Polyelectrolyte Multilayers with a Tunable Young's Modulus: Influence of Film Stiffness on Cell Adhesion," Langmuir 22(3):1193-1200.
Schneider et al. (2007) "Multifunctional Polyelectrolyte Multilayer Films: Combining Mechanical Resistance, Biodegradability, and Bioactivity," Biomacromolecules 8(1):139-145.
Schoeler et al. (2003) "Growth of Multilayer Films of Fixed and Variable Charge Density Polyelectrolytes: Effect of Mutual Charge and Secondary Interactions," Macromolecules 36(14):5258-5264.
Schuler et al. (2001) "Decomposable Hollow Biopolymer-Based Capsules," Biomacromolecules 2:921-926.
Segura et al. (2002) "Surface-Tethered DNA Complexes for Enhanced Gene Delivery," Bioconjugate Chem. 13(3):621-629.
Serizawa et al. (2002) "Thermoresponsive Ultrathin Hydrogels Prepared by Sequential Chemical Reactions," Macromolecules 35(6):2184-2189.
Serizawa et al. (2003) "Time-Controlled Desorption of Ultrathin Polymer Films Triggered by Enzymatic Degradation," Angew Chem. Int. Ed. 42(10):1115-1118.
Shea et al. (1999) "DNA Delivery from Polymer Matrices for Tissue Engineering," Nat. Biotechnol. 17:551-554.
Shetty et al. (1980) "Ready Separation of Proteins from Nucleoprotein Complexes by reversible Modification of Lysine Residues," Biochem. J. 191:269-272.
Shim et al. (2008) "Controlled Delivery of Plasmid DNA and siRNA to Intracellular Targets Using Ketalized Polyethylenimine," Biomacromolecules 9(2):444-455.
Such et al. (2006) "Assembly of Ultrathin Polymer Multilayer Films by Click Chemistry," J. Am. Chem. Soc. 128(29):9318-9319.
Suh et al. (Apr. 1, 2003) "Efficient Active Transport of Gene Nanocarriers to the Cell Nucleus," Proc. Nat. Acad. Sci. USA 100(7):3878-3882.
Sukhishvili et al. (2000) "Layered, Erasable, Ultrathin Polymer Films," J. Am. Chem. Soc. 122(39):9550-9551.
Sukhishvili et al. (2002) "Layered, Erasable Polymer Multilayers Formed by Hydrogen-Bonded Sequential Self-Assembly," Macromolecules 35(1):301-310.
Sukhishvili, S.A. (2005) "Responsive Polymer Films and Capsules via Layer-by-Layer Assembly," Curr. Opin. Colloid. Interface Sci. 10:37-44.
Sun et al. (2000) "Covalently Attached Multilayer Assemblies by Sequential Adsorption of Polycationic Diazo-Resins and Polyanionic Poly(acrylic acid)," Langmuir 16(10):4620-4624.
Sun et al. (2007) "Assembly of Multilayers Films Using Well-Defined, End-Labeled Poly (acrylic Acid): Influence of Molecular Weight on Exponential Growth in a synthetic Weak Polyelectrolyte System," Langmuir 23(16):8452-5459.
Takahashi et al. (2003) "Transgene Delivery of Plasmid DNA to Smooth Muscle Cells and Macrophages from a Biostable Polymer-Coated Stent," Gene Ther. 10:1471-1478.
Takahashi et al. (2007) "Delivery of Large Biopharmaceuticals from Cardiovascular Stents: An Alternative Strategy for Inhibition of Restenosis," Biomacromolecules 8(11):3281-3293.
Tang et al. (2006) "Biomedical Applications of Layer-by-Layer Assembly: From Biomimetics to Tissue Engineering," Adv. Mater. 18(24):3203-3224.
Thomas et al. Nov. 12, 2002) "Enhancing Polyethylenimine's Delivery of Plasmid DNA into Mammalian Cells," Proc. Nat. Acad. Sci. USA 99(23):14640-14645.
Vazquez et al. (Nov. 27, 2002) "Construction of Hydrolytically-Degradable Thin Films via Layer-by-Layer Deposition of Degradable Polyelectrolytes," J. Am. Chem. Soc. 124(47):13992-13993.
Verma et al. (Sep. 18, 1997) "Gene Therapy—Promises, Problems and Prospects," Nature 389:239-242.
Veron et al. (2004) "New Hydrolyzable pH-Responsive Cationic Polymers for Gene Delivery: A Preliminary Study," Macromol. Biosci. 4(4):431-444.
Walter et al. (2004) "Local Gene Transfer of phVEGF-2 Plasmid by Gene-Eluting Stents: An Alternative Strategy for Inhibition of Restenosis," Circulation 110:36-45.
Wang et al. (2001) "A Novel Biodegradable Gene Carrier Based on Polyphosphoester," J. Am. Chem. Soc. 123:9480-9481.
Wolff et al. (Dec. 2001) "Nuclear Security Breached," Nat. Biotechnol. 19:1118-1120.
Wolff, J.A. (Aug. 2002) "The 'Grand' Problem of Synthetic Delivery," Nat. Biotechnol. 20:768-769.
Wood et al. (2005) "Tunable Drug Release from Hydrolytically Degradable Layer-by-Layer Thin Films," Langmuir 21:1603-1609.
Wood et al. (2006) "Controlling Interlayer Diffusion to Achieve Sustained, Multi-Agent Delivery from Layer-by-Layer Films," Proc. Nat. Acad. Sci. USA 103:10207-10212.
Wu et al. (Oct. 1, 2002) "Cell-Biological Applications of Transfected-Cell Microarrays," Trends Cell Biol. 12(10):485-488.

(56) References Cited

OTHER PUBLICATIONS

Wu, G.and Xi Zhang (2010) "Unconventional Layer-by-Layer Assembly for Functional Organic Thin Films, Polymer Thin Films," Abbass A Hashim (Ed.), ISBN: 978-953-307-059-9, InTech, Available from: http://www.intechopen.com/books/polymer-thin-films/unconventional-layer-by-layer-assembly-for-functional-organic-thin-films.

Xie et al. (Jan. 5, 1999) "Design of Reactive Porous Polymer Supports for High Throughput Bioreactors: Poly(2-vinyl-4,4-dimethylazlactone-co-acrylamide-coethylene dimethacrylate) Monoliths," Biotechnol. Bioeng. 62(1):30-35.

Xu et al. (Jun. 25, 2007) "Targeted Charge-Reversal Nanoparticles for Nuclear Drug Delivery," Angew Chem. Int. Ed. 46(26):4999-5002.

Yang et al. (2002) "Micropatterning of Polymer Thin Films with pH-Sensitive and Cross-Linkable Hydrogen-Bonded Polyelectrolyte Multilayers," J. Am. Chem. Soc. 124(10):2100-2101.

Yin et al. (1998) "Architectural Copolymers: Rod-Shaped, Cylindrical Dendrimers," J. Am. Chem. Soc. 120:2678-2679.

Zelikin et al. (2003) "Competitive Reactions in Solutions of Poly-L-histidine, Calf Thymus DNA, and Synthetic Polyanions: Determining the Binding Constants of Polyelectrolytes," J. Am. Chem. Soc. 125:13693-13699.

Zelikin et al. (2006) "Disulfide Cross-Linked Polymer Capsules: En Route to Biodeconstructible Systems," Biomacromolecules 7(1):27-30.

Zhang et al. (2002) "Ways for Fabricating Stable Layer-by-Layer Self-Assemblies: Combined Ionic Self-Assembly and Post Chemical Reaction," Colloid Surface A 198:439-442.

Zhang et al. (2003) "Fabrication of Stable Hollow Capsules by Covalent Layer-by-Layer Self-Assembly," Macromolecules 36(11):4238-4240.

Zhang et al. (2004) "Multilayered Thin Films that Sustain the Release of Functional DNA under Physiological Conditions," Langmuir 20(19):8015-8021.

Zhang et al. (2006) "Erosion of Multilayered Assemblies Fabricated from Degradable Polyamines: Characterization and Evidence in Support of a Mechanism that Involves Polymer Hydrolysis," J. Poly. Sci. A Poly. Chem. 44:5161-5173.

Zhang et al. (2006) "Structure/Property Relationships in Erodible Multilayered Films: Influence of Polycation Structure on Erosion Profiles and the Release of Anionic Polyelectrolytes," Langmuir 22:239-245.

Zhang et al. (2006) Multilayered Films Fabricated from Combinations of Degradable Polyamines: Tunable Erosion and Release of Anionic Polyelectrolytes, Macromolecules 39:8928-8935.

Zhang et al. (2007) "Multilayered Films Fabricated from Plasmid DNA and a Side-Chain Functionalized Poly(Beta-amino ester): Surface-Type Erosion and Sequential Release of Multiple Plasmid Constructs from Surfaces," Langmuir 23:11139-11146.

Zhang et al. (2007) "Ultrathin Multilayered Films Assembled from 'Charge-Shifting' Cationic Polymers: Extended, Long-Term Release of Plasmid DNA from Surfaces," Adv. Mater. 19:4218-4223.

Zhou et al. (1990) "Preparation of Poly(L-serine ester): A Structural Analog of Conventional Poly(L-serine)," Macromolecules 23(14):3399-3406.

Ziauddin et al. (May 3, 2001) "Microarrays of Cells Expressing Defined cDNAs," Nature 411:107-110.

\* cited by examiner

ANIONIC CHARGE-DYNAMIC POLYMERS FOR RELEASE OF CATIONIC AGENTS

CROSS-REFERENCE TO RELATED APPLICATIONS

This application claims priority to U.S. application Ser. No. 12/479,582, filed Jun. 5, 2009 which in turn claims the benefit of U.S. provisional application Ser. No. 61/059,194, filed Jun. 5, 2008. Each of these applications is incorporated by reference in its entirety herein.

STATEMENT REGARDING FEDERALLY SPONSORED RESEARCH

This invention was made with government support under EB002746 and EB006820 awarded by the National Institutes of Health. The government has certain rights in the invention.

BACKGROUND OF THE INVENTION

The present invention relates to dynamic charge state anionic polymers that are useful for release of cationic molecules, polyelectrolyte multilayers fabricated from them and methods of using the polymers.

Methods for the layer-by-layer assembly of multilayered polyelectrolyte films (or 'polyelectrolyte multilayers') provide nanometer-scale control over the structures and compositions of thin films fabricated from a broad range of cationic and anionic polymers.[1-4] An evolving understanding of the structures and properties of these multilayered materials— and the ways that they can be manipulated at various length scales—has contributed to the design of functional thin films of interest in a growing number of fundamental and applied contexts.[3-10]

Owing to the polyvalent nature of the electrostatic interactions in polyelectrolyte multilayers, these assemblies are frequently regarded to be 'stable' in physiologically relevant environments, i.e., the assemblies often do not dissolve readily or undergo large changes in macroscopic film properties when incubated in physiological media.[3,5,7,9] This general stability confers several potential practical advantages, and has contributed significantly to the development of polyelectrolyte multilayers in biomedical and biotechnological contexts.

The present invention relates to certain polyelectrolyte multilayers and methods that can be used to disrupt electrostatic interactions in such multilayers and promote the controlled disassembly of the multilayers in aqueous media.[8,10] Methods that provide such control facilitate the development of thin films and coatings that permit the release of precise and well-defined quantities of chemical or biological agents from the surfaces of macroscopic, microscopic, or nanoscopic objects. The present invention provides a new approach to the design of polyelectrolyte multilayers that provides control over film erosion and the release of cationic agents from film-coated surfaces.

Several past studies have reported that it is possible to design polyelectrolyte multilayers that erode, degrade, or disassemble in aqueous environments by fabricating them using polyelectrolytes with functionality that can be cleaved or degraded, for example, either hydrolytically,[11-16] enzymatically,[17-19] or reductively.[20,21] The incorporation of degradable polyelectrolytes permits tunable and/or triggered control over film disassembly and can be used to design films that provide control over the release of a variety of different agents.[11-21] Additional details on these and other past approaches to promoting film disruption can be found in several recent reviews.[8,10] The majority of past reports on the incorporation of degradable polymers into multilayered films have focused on the use of degradable cationic polymers and thus, in general, on films designed to erode and control the release anionic polyelectrolytes (e.g., DNA).[8,10]

In principle, the fabrication of polyelectrolyte multilayers using degradable anionic polymers would provide a platform for the design of thin films that permit control over the release of cationic agents (e.g., cationic proteins, peptides, polymers, nanoparticles, etc.). There have been reports that enzymatically degradable anionic polymers can be used to fabricate multilayers that degrade in the presence of specific enzymes[17,22] or upon contact with cells.[17,23] Progress toward the fabrication of films using hydrolytically degradable anionic polymers, however, has been limited by the dearth of commercially available synthetic polymers that are both anionic and degradable, and, more generally, by the challenges associated with the synthesis of such polymers. Thus, there is a need in the art for synthetic polymers that are anionic and degradable.

It has been reported[24-29] recently that it is possible to design 'charge-shifting' cationic polymers (that is, cationic polymers that undergo dynamic reductions in their net charge, which can also be called charge-dynamic polymers) by designing polymers inter alia with amine-functionalized side chains that can be cleaved hydrolytically. Polymer 1 (Eq 1) presents an example of this approach;[24] this polymer undergoes a gradual reduction in net charge (e.g., from cationic to anionic) upon side chain hydrolysis. Polymer 1 can, for example, be used to fabricate multilayers that release plasmid DNA (negatively charged species) for up to three months.

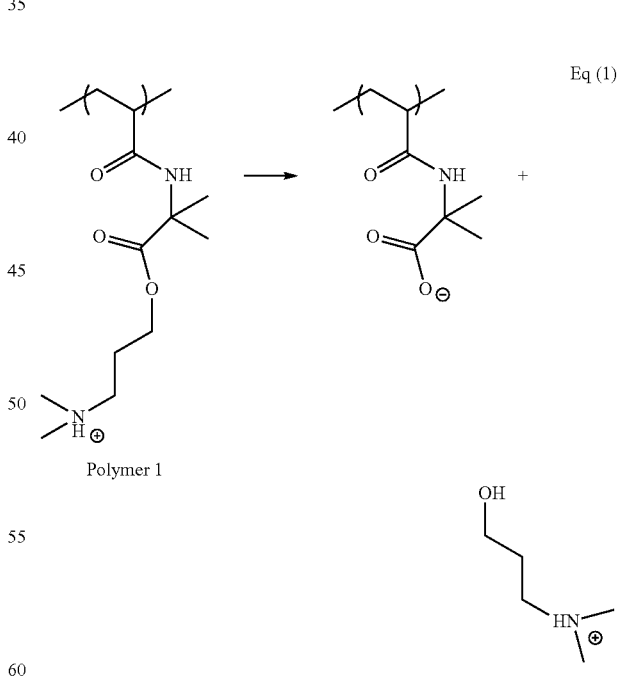

Polymer 1

Both film erosion and the release of DNA from mulitlayers containing polymer 1 can be understood in terms of disruptions in the ionic interactions in these assemblies that occur upon polymer side chain hydrolysis.[24] Published US patent application 2005/0027064 published Feb. 3, 2005 relates to charge-dynamic polymers and delivery of anionic compounds and provides additional examples of charge-dynamic polymer structures and their applications.

SUMMARY OF THE INVENTION

The present invention provides materials and methods for the generation of multilayers that erode and release cationic film components. This approach is based on the design of charge-dynamic anionic polymers.

The present invention provides dynamic charge state anionic polymers, or more simply polymers, that include a polymeric backbone formed from one or more different monomers. One or more removable functional group(s) is/are attached to one or more repeat units of the polymeric backbone. The dynamic charge state anionic polymer has an anionic charge density which is a characteristic of the polymeric backbone and the functional group or groups attached to the polymeric backbone. The net charge of the dynamic charge state anionic polymer increases when one or more of the removable functional group(s) is/are removed from the dynamic charge state anionic polymer. The present polymers can also be part of a copolymer where one or more segments of the copolymer are the dynamic charge state anionic polymer.

In specific embodiments, the polymer contains side chains having removable functional groups as defined herein, for example, amide side chains. In specific embodiments, polymers that have amide side chains can be synthesized from polymers having amine side chains, including, among others, poly(allyl amine), poly(vinyl amine), poly(ethylene imine), poly(lysine), poly(amidoamine)dendrimers, and chitosan into which amide side chains can be introduced. The polymeric backbone can be linear, branched or hyperbranched.

In some embodiments, at least one of the one or more removable functional group(s) is a hydrolysable group, such as a pendant amide. The one or more removable functional group(s) may also include a labile linkage, such as an ester, an anhydride, an orthoester, a phosphoester, or an acetal. More specifically, the one or more removable functional groups are hydrolysable under acidic conditions. The anionic polymer may contain one or more different amide side groups or a mixture of side groups of various chemical structure wherein at least a portion (at least 10 mol percent) of the side chains are amides.

In some embodiments, the polymer with amide side chains is a block of a copolymer containing two or more blocks and the other blocks have different, polymer backbones. In some embodiments, the polymer of the invention is a copolymer, including a block copolymer, comprising portions with different amide side chains. In other embodiments, the polymer of the invention is a copolymer, including a block copolymer, comprising two or more different repeat units with different polymer side chains of which at least one side chain is an amide side chain. In specific embodiments, the polymer of the invention is a copolymer, including a block copolymer, comprising two or more different repeat units where the two or repeat units include those having different amide side chains which hydrolyze at different rates on contact with an acidic environment.

In some embodiments, the polymers of the invention are biodegradable and biocompatible.

In the polymers of the present invention, the mole percent of the repeat units comprising the polymeric backbone which are substituted with the one or more removable functional group(s) range from 10 to 100 percent or from about 10 percent to about 100 percent. In additional embodiments, the mole percent of the repeat units substituted with a removable functional group may range from about 30 percent to about 100 percent, about 50 percent to about 100 percent or about 70 percent to about 100 percent. In specific embodiments, the polymers of the present invention can on average have 5 or more repeating units. In additional specific embodiments, the polymers of the invention have 5 to several hundred thousand repeating units. In more specific embodiments, polymers of this invention have from 5-500,000 repeating units, from 5-300,000 repeating units, from 5-200,000 repeating units or from 5-100,000 repeating units. The polymers of the present invention may have any desired molecular weight, such as from 1,000 to 100,000 grams/mole, or from about 2,000 to 50,000 grams/mole.

The dynamic charge state anionic polymer can be associated with a ligand facilitating the delivery of the polymer to a specific target, such as a target cell.

The present polymers can be part of a copolymer, which can be composed of any other polymers, for example a polymer such as PEG or PEO, which are commonly used to give stability toward protein adsorption. The present polymer is generally anionic, but different functional groups attached to the polymer can render the polymer zwitterionic. To impart an anionic charge to the polymer, the attached functional groups are negatively charged. The present polymer may also be capable of buffering changes in pH which result from the make-up of the polymer backbone and/or the attached functional groups.

The present dynamic charge state anionic polymers may be non-immunogenic, non-toxic or both nonimmunogenic and non-toxic. In the present polymers, the polymeric backbone can be degradable or nondegradable. The present polymers do not require that any degradation of the backbone occur at the same time as the shift in anionic charge.

One skilled in the art will recognize that the measure of degradability will be commensurate with the environmental conditions and desired properties for any particular application for the present polymers. As one non-limiting example, for biomedical uses of the present polymers, the present invention contemplates polymers that degrade in a desired time frame (from an hour to a week to a month to a year) under physiological conditions typically found in the body or in a cell or cell compartment (e.g., pH ranges from about 5.0 to 7.4, a temperature of about 37° C.) and an ionic strength of a typical physiological solution (generally around 130-150 mM NaCl, for example). In the present invention, the degradability of the polymer can be measured by a variety of methods, including, but not limited to, GPC (gel permeation chromatography).

The present invention provides polyelectrolyte multilayers which comprise at least one layer which is formed from a dynamic charge state anionic polymer of the invention or from a copolymer containing them. The polyelectrolyte multilayers comprise at least one and preferably more than one layer formed from a dynamic charge state anionic polymer of this invention. The polyelectrolyte multilayers in addition may contain layers formed from polymers other than dynamic charge state anionic polymers. For example, the polyelectrolyte multilayers may contain one or more layers formed from cationic polymers, anionic polymers, neutral polymers or zwitterionic polymers in addition to one or more layers formed from dynamic charge state anionic polymers. The polyelectrolyte multilayer may contain an agent that is intended to be selectively released from the polyelectrolyte multilayer. That agent may be neutral, zwitterionic, anionic or cationic and in specific embodiments is cationic. The agent may be a therapeutic agent or a diagnostic agent and may be selected among others from protein, peptide, and small molecules.

In specific embodiments, polyelectrolyte multilayers of this invention comprise a plurality of cation/anionic polymer bilayers, particularly wherein one or more cations or other encapsulated species are to be released. In specific embodiments, bilayers containing an active agent to be released are optionally separated by one or more intermediate polyelectrolyte bilayers which do not contain an active ingredient to be released. Each polyelectrolyte multilayer of the invention can optionally comprise one or more top protective bilayers and/or one or more base bilayers. One or more base bilayers can be formed, for example, between a substrate surface and an cation/anionic polymer bilayer where the cation or cations therein are intended for controlled release. A plurality of such base layers may intervene between the substrate surface and any cation/anionic polymer bilayers. Base layers, if present, are the bottom most layers in a polyelectrolyte assembly (those closest to the substrate or surface). An intermediate bilayer or a plurality of intermediate layers may intervene between bilayers or pluralities of bilayers of cation/anionic polymers where the cation or cations are intended for controlled release. One or more top protective bilayers can be positioned as the top most bilayers in a polyelectrolyte multilayer. Intermediate, top protective and base bilayers can comprise a anionic polymer of the invention and a cation (including a cationic polymer) other than a cation, the release of which is intended to be controlled. Intermediate, top protective and base bilayers can comprise a anionic or cationic polymer other than those specifically described in the formulas herein, but which is degradable.

Polyelectrolyte multilayers can comprise a plurality of bilayers containing different cations or different anionic polymers. The layers containing the same or different cationic or anionic components can be ordered in a variety of ways in the multilayer. For example, a plurality of layers having the same cations and anionic polymers can be ordered sequentially in the multilayer. Alternatively, two or more layers containing different cationic or different anionic components can be layered sequentially in the multilayer.

The invention provides methods of forming such polyelectrolyte multilayers comprising a dynamic charge state anionic polymer. The invention further provides methods of disrupting such polyelectrolyte multilayers by selectively changing the net charge of the dynamic charge state anionic polymer in the polyelectrolyte multilayer. The invention additionally provides methods for release of one or more agents, particularly therapeutic agents or diagnostic agents, from such polyelectrolyte multilayers by selective disruption of the polyelectrolyte multilayer by selectively changing the net charge of the dynamic charge state anionic polymer. A selective change in the net charge of the dynamic charge state anionic polymer can be obtained by selective removal of one or more anionic side chains of the dynamic charge state anionic polymer.

The present invention also provides the present polymers complexed with one or more cationic agents thereby forming an interpolyelectrolyte complex. Suitable cationic agents may be naturally-occurring, synthetic, or both. In some embodiments, suitable examples of cationic agents include proteins and polypeptides. In other embodiments, the cationic molecule or agent may be a therapeutic molecule or a diagnostic molecule, and/or may be selected from a protein, peptide or small molecule.

The interpolyelectrolyte complex may have any desired size depending upon the intended use of the interpolyelectrolyte complex. For example, when the interpolyelectrolyte complex is used for delivery of a cationic agent to a cell, the interpolyelectrolyte complex can be 50 nm to about 400 nm, or from about 50 to about 250 nanometers, in size. In other embodiments, the interpolyelectrolyte complex may be provided in a layered complex made up of one or more layers of the dynamic charge state anionic polymer and one or more layers of the cationic agent.

Generally, the interpolyelectrolyte complex will be prepared by mixing the dynamic charge state anionic polymer with the cationic agent, thereby allowing formation of the interpolyelectrolyte complex.

In some embodiments, the present polymer or interpolyelectrolyte complex may be provided in a biologically compatible solution or a biological solution. Further, the polymer may be provided with a pharmaceutically acceptable excipient or another completely different polymer (e.g., another anionic polymer) which could be an "excipient" or could have an added function. Accordingly, the present compounds include pharmaceutical compositions that include any of the polymers or mixtures described herein.

The present invention also provides methods for controlled delivery or release of an agent which may be a therapeutic or diagnostic agent and in specific embodiments is a cationic agent. In specific embodiments, controlled delivery or release may be to a cell or tissue. Controlled release or delivery may be from a polyelectrolyte multilayer of this invention or from an interpolyelectrolyte complex of this invention. Release or delivery of the agent is controlled by selective change in the net charge of a dynamic charge state anionic polymer as described herein.

In the present methods, the target cell or tissue can be in vitro or in vivo. Where the target cell or tissue is in vivo, the polyelectrolyte multilayer or the interpolyelectrolyte complex may be administered to a mammal, including a human. Any suitable form of administration may be employed. In some embodiments of the present methods, the tissue or cell is a eukaryotic cell. In specific embodiments, the tissue or cell is that of a mammal, including a human.

In the present methods and polymers, removal of the one or more of the removable functional group(s) from the dynamic charge state anionic polymer may be at least partially hydrolytic, partially enzymatic and/or partially photolytic removal. In a specific embodiment, removal of the one or more removable functional groups is not enzymatic. In a specific embodiment, removal of the one or more removable functional groups is hydrolytic. The present polymers and methods may also be designed so that the removal of the one or more of the removable functional group(s) from the dynamic charge state anionic polymer occurs at a substantially constant rate or does not occur at a constant rate.

The present invention also provides kits containing one or more polymers of this invention in combination with one or more of one or more cationic species for inclusion in polyelectrolyte multilayers and delivery to a target cell or tissue, one or more substrates upon which polyelectrolyte multilayers may be formed; one or more media for facilitating formation of polyelectrolyte multilayers; media and/or reagent for triggering hydrolytic, enzymatic or other removal of removal functional groups; or instructions for carrying out formation of multilayers and/or degradation of multilayers. Kits may include one or more individual containers having a selected amount of the one or more anionic charge dynamic polymers of the invention to carry out a desired application for delivery of a desired cationic species. Kits may include one or more individual containers having a selected amount of one or more cationic species for inclusion in polyelectrolyte multilayers and for release from such multilayers.

The invention also provides methods of preparing the polymers of the invention and pharmaceutical compositions containing the polymers and one or more therapeutic, diagnostic, and/or prophylactic agent.

In yet another aspect of the invention, the polymers of this invention are used to form nanometer-scale complexes with cationic agents.

In another aspect of the invention, the polymers are used to encapsulate therapeutic, diagnostic, and/or prophylactic agents. In other embodiments, the polymers of this invention are employed to coat (e.g., to form one or more layers on) particles, including microparticles and nanoparticles. This coating of particles can include the formation of polyelectrolyte multilayers on microparticles or nanoparticles. Hollow multilayer capsules can also be formed employing one or more dynamic charge state anionic polymers of this invention. Microcapsules and/or nanocapsules can be formed by initial formation of a multilayer or polyelectrolyte multilayer comprising a dynamic charge state anionic polymer on a sacrificial particle, either microparticle or nanoparticle, which serves as a template. The sacrificial particle is thereafter degraded, as is known in the art, leaving the microcapsule. The coated microparticles and capsules can range from 1 micrometer to 500 micrometers, for example. Coated nanoparticles are generally less than 1 micron. In some such embodiments, the coated particles or capsules allow for the delivery of small molecules, proteins, and/or peptides. Microparticles and nanoparticles may be prepared using any of the techniques known in the art to make such particles, such as, for example, double emulsion and spray drying. In some embodiments, coated particles and hollow capsules may be used for pH-triggered delivery of the encapsulated contents due to the pH-responsive nature of the polymers.

In another aspect of the invention, the polymers are used to encapsulate a cationic agent which is to be delivered selectively in response to a trigger or delivered in a controlled manner over time. The cationic agent can for example be comprised in a multilayer film which also comprises one or more anionic charge dynamic polymers of this invention. In a specific embodiment, the cationic agent can be released from the film on contact with an environment of appropriate pH, e.g., acidic pH. The contact with the environment may be contact with an aqueous solution of appropriate pH.

DETAILED DESCRIPTION OF THE INVENTION

Figure 1:
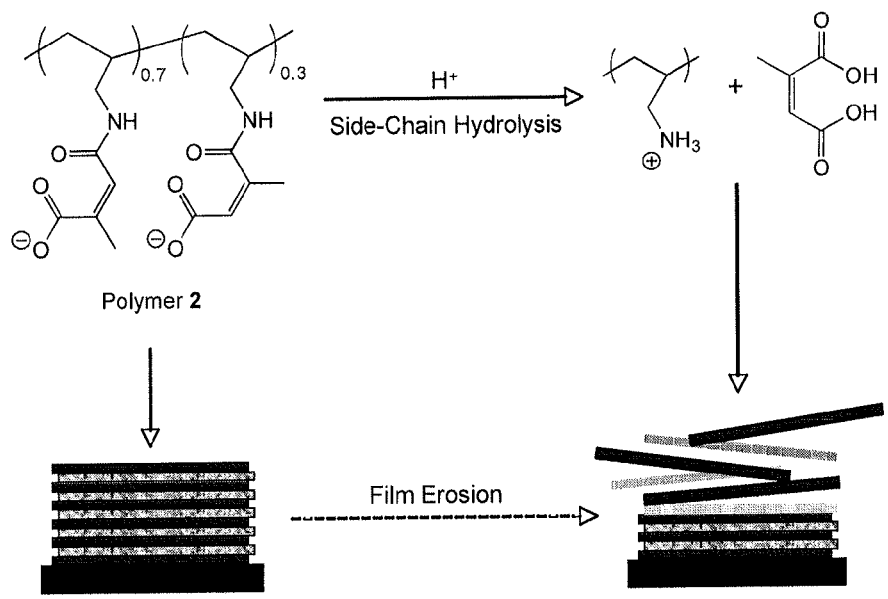
FIG. 1: Exemplary illustration of the method of this invention for controlled film erosion. Top: Hydrolysis of the citraconic amide side chains of anionic 'charge-shifting' polymer 2 under acidic conditions yields cationic poly(allylamine). Bottom: Polymer 2 (grey) is anionic and can be used to fabricate polyelectrolyte multilayers. Time-dependent changes in the net charge of polymer 2 result in changes in the nature of the ionic interactions in the multilayers and promote film disruption and the release of cationic film components (red). Polymer 2 and PAH are shown as being completely ionized for illustrative purposes (see text).

The general approach of the present invention is based on the synthesis of anionic polymers that undergo dynamic changes in charge states (i.e., from anionic to "less anionic" or to zwitterionic or cationic) to trigger the disruption of multilayers and/or interpolyelectrolyte complexes and the release of agents (particularly therapeutic or diagnostic agents), including among others, proteins, peptides, polymers or nanoparticles which may be cationic.

In one embodiment, the invention makes use of methods developed for the reversible conversion of amine functionality to carboxylic acid functionality by treatment with α-methyl derivatives of maleic anhydride.[30-36] Past studies have demonstrated, for example, that the addition of citraconic anhydride (10) to primary amines results in the formation of a citraconic amide, and that citraconic amides can be hydrolyzed readily under acidic conditions to regenerate primary amine functionality (Eq 2).[30]

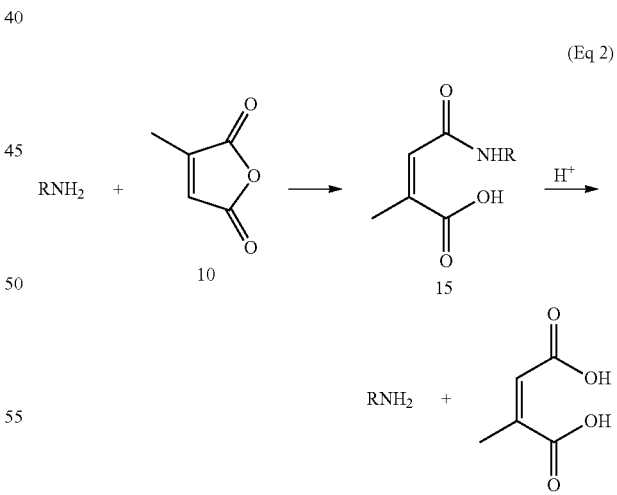

While the hydrolysis of amide bonds in aqueous media generally occurs very slowly, the hydrolysis of citraconic amides (e.g., 15) occurs rapidly under acidic conditions owing to intramolecular catalysis facilitated by the neighboring carboxylic acid group, which is maintained in close proximity to the amide bond by the conformational rigidity of the nearby double bond.[30,31] The kinetics and mechanism of this reaction have been investigated using small-molecule model systems,[30,31] and this general approach has been applied to the chemical modification of proteins (e.g., by reaction with surface-accessible lysine residues) as a means to reversibly manipulate protein charge.[37-39]

Anionic polymers of the invention can be generated generally by the reaction of small-molecule anhydrides with amine side chains on a polymer backbone. In specific embodiments, anionic polymers of the invention are prepared by the reaction of anhydrides of formulas I-IV, below, with primary amine side chains on a polymer backbone,

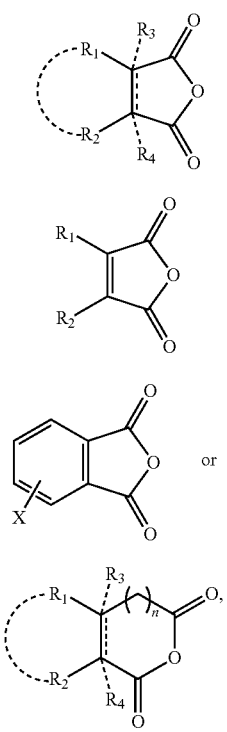

where n is 0 or 1 and where dotted lines indicate optional bonds, if $R_3$ and $R_4$ are absent the bond in the ring is a double bond; and where $R_1$, $R_2$, and $R_3$ and $R_4$ (if present) are not particularly limited except that these groups should not significantly interfere with the ability of the anhydride to react with primary amines and further that these groups should not contain cationic moieties which decrease the anionic charge state of the polymer. In specific embodiments, $R_1$, $R_2$, and $R_3$ and $R_4$ are selected from optionally substituted alkyl, alkenyl, alkynyl, aryl, heteroaryl, carbocyclic and heterocyclic groups. In addition, $R_1$ and $R_2$ can together form a 5-10 member carbocyclic or heterocyclic ring which may be aryl or heteroaryl or which can contain one or two double bonds. X represents substitution on the indicated ring with one to four substituents selected from hydrogen, halogen, hydroxyl, alkyl, alkenyl, alkynyl, aryl, heteroaryl, carbocyclic or heterocyclic groups and two X substituents can together form a 5-10 member carbocyclic or heterocyclic ring which may be aryl or heteroaryl or which can contain one or two double bonds. $R_1$, $R_2$, and $R_3$ and $R_4$ groups and X substituents which are alkyl, alkenyl, alkynyl, aryl, heteroaryl, carbocyclic or heterocyclic groups are optionally substituted with one or more halogens, hydroxyl, —CN, alkoxyl, —COOH (or —COO⁻), —COOR, or —CON(R')₂, where R is alkyl, alkenyl, alkynyl, aryl, heteroaryl, carbocyclic or heterocyclic and each R' is hydrogen or R.

In specific embodiments, $R_3$ and $R_4$ are absent and the indicated ring contains a double bond. In further embodiments, $R_1$-$R_4$ are optionally substituted alkyl groups. In further embodiments, $R_3$ and $R_4$ are absent, the indicated ring contains a double bond and $R_1$ and $R_2$ are optionally substituted alkyl groups. In further embodiments, $R_3$ and $R_4$ are absent, the indicated ring contains a double bond, one of $R_1$ or $R_2$ is a hydrogen and the other of $R_1$ or $R_2$ is an optionally substituted alkyl group. In a specific embodiment, X represents hydrogen substitutents on the indicated ring. In a specific embodiment, X represents one to four halogen substituents on the indicated ring. In a specific embodiment, n is 1. In another specific embodiment, n is 1, $R_3$ and $R_4$ are absent and the indicated ring contains a double bond. In another specific embodiment, n is 1, $R_3$ and $R_4$ are absent, the indicated ring contains a double bond and $R_1$ and $R_2$ are optionally substituted alkyl groups. In specific embodiments one or both of $R_1$ and $R_2$ are methyl groups.

In specific embodiments, the anionic polymers of this invention comprise amide side chains which carry a double bond as illustrated in formulas V, VI, VII and polymer 2. Reaction of the anhydride with a polymer or copolymer having primary amine functionality results in the formation of side chain amides and presents a straightforward and modular approach to the generation of 'charge-shifting' anionic polymers, or anionic polymers capable of undergoing changes in net charge (i.e., from net anionic to neutral or net cationic) upon side chain amide hydrolysis.

Several recent reports have demonstrated the application of this approach to the design of polymer-based carrier systems for the delivery of nucleic acids,[32,34,35] proteins,[33] or small molecules[36] that create disruptive electrostatic interactions,[33,36] unmask other disruptive functionality,[32,34,35] or shed functionality that is no longer needed[35] upon exposure to low pH environments (e.g., such as those found in cell endosomes or lysosomes or other extracellular environments).

In specific embodiments, the invention provides anionic polymers of formula V:

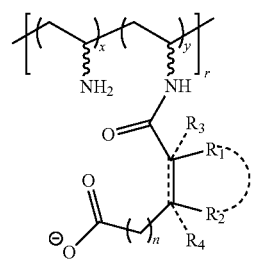

where r is an integer ranging from 5 to 100,000, x and y are numbers representing the mole percent of the indicated side chains in the polymer where y represents from 10 to 100 mole percent of amide side chain and x+y is 1. Additionally $R_1$-$R_4$, n and dotted lines are as defined above and the wavy line represents a linker which covalently attaches the primary amine or the amide to the polymer backbone. Note also that the polymer can contain one or more than one different amide side chains. The number y represents the total mole percent of amide side chains e.g., y1+y2+y3+y4 ... +yn, where y1 to yn represent the individual mole percent of different amide side chains. When there are more than one different amide side chains the variables $R_1$-$R_4$ in the different amides can be different, n may be different or the optional double bond in the amide may be present or absent. In specific embodiments, all amide side chains in the polymer are the same. In other specific embodiments, there are two or more different amide side chains. In additional embodiments, there are two, three, four, five or six different amide side chains. In other specific embodiments, there are two different amide side chains which are stereoisomers of each other. In specific embodiments, y ranges from 0.1 to 0.3 (from 10-30 mole percent). In other embodiments, y ranges from 0.20 to 0.5 representing 20 to 50 mole percent. In additional embodiments, y ranges from 25 to 100 mole percent. In other embodiments, y is 100 mole percent.

The primary amine or amide is linked to the polymer backbone by a linker moiety which in specific embodiments is an alkylene, or alkyleneoxy linker containing from 1 to 10 carbon atoms. In a specific embodiment, the linker is an alkylene linker. In a specific embodiment, the linker is an alkylene linker of formula —$(CH_2)_m$—, where m is an integer that ranges from 1 to 10 and preferably ranges from 1 to 6 and in specific embodiments is 1, 2 or 3. In a specific embodiment, the linker is an alkyleneoxy linker of formula —$(CH_2)_{m1}$—O—$(CH_2)_{m2}$—, —$(CH_2)_{m1}$—O—$(CH_2)_{m2}$—O—$(CH_2)_{m3}$—, —$(CH_2)_{m1}$—O—$(CH_2)_{m2}$—O—$(CH_2)_{m3}$—O—$(CH_2)_{m4}$—, or —$(CH_2)_{m1}$—O—O—$(CH_2)_{m2}$—O—$(CH_2)_{m3}$—O—$(CH_2)_{m4}$—O$(CH_2)_{m5}$—, where m1, m2, and m3, m4, and m5, if present, are integers and m1+m2+m3+m4+m5=2-10. In more specific embodiments, m1 and m2 and m3, m4, and m5, if present, are the same; m1 and m2 and m3, m4, and m5, if present are all 2 or all 3 or all 4; or m1 and m2 and m3, m4, and m5, if non-zero, are different.

The polymer of formula V is a generic formula for an initially anionic charge dynamic polymer of this invention in which the charge can be shifted from anionic, to zwitterionic, to cationic, by hydrolysis of amide groups. These anionic charge dynamic polymers can be used to destabilize polyelectrolyte multilayers and promote the release of agents, particularly cationic agents, from surfaces coated with the multilayers in aqueous media. The hydrolysis can be triggered by decreasing the pH of the medium to which the multilayers or the polymer is contacted.

In a more specific embodiment, the invention provides polymer VI and even more specifically polymer 2.

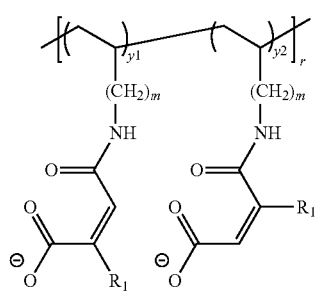

VI where r, y1, y2, m and $R_1$ are as defined above. In a specific embodiment of formula VI, $R_1$ is selected from optionally substituted alkyl or phenyl groups. In more specific embodiments, $R_1$ is an unsubstituted alkyl group having 1 to 6 carbon atoms or having 1 to 3 carbon atoms. In a specific embodiment, y1 ranges from 0.1 to 0.9. In another embodiment, y1 ranges from 0.25 to 0.75. In another embodiment, y1 ranges from 0.60 to 0.80. In specific embodiments y1/y2 is 2 to 3. In specific embodiments, y1/y2 is 2.3.

In another embodiment, the invention provides polymer VII:

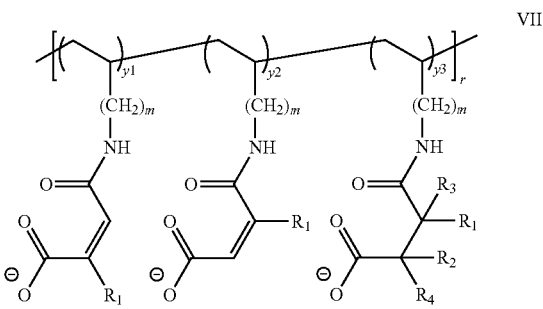

VII where r, m, and $R_1$ are as defined above and y1, y2 and y3 are numbers representing the mole percent of the indicated side group where y1+y2+y3 is 1; In a specific embodiment, $R_1$ is an optionally substituted C1-C6 alkyl group. In another specific embodiment m is 1-6 or m is 1, 2 or 3. In specific embodiments y3 ranges from 0.01 to 0.90, y3 ranges from 0.25 to 0.50 or y3 ranges from 0.1 to 0.25. In specific embodiments y1/y2 is 2 to 3. In specific embodiments, y1/y2 is 2.3.

In specific embodiments, the polymer of the above formulas is a block of a block copolymer. In specific embodiments, the copolymer comprises one or more blocks of PEG or PEO.

In specific embodiments, the polymers of the above formulas are employed to form multiple layer polyelectrolyte films. Each layer of such films comprises a bilayer comprising one or more cations and one or more anionic polymers. In a specific embodiment, the one or more than one of the cations can be a cationic polymer. In a specific embodiment, a bilayer can comprise a plurality of cations each carrying 1-4 positive charges for each anionic polymer of this invention therein. In a specific embodiment, a bilayer can comprise a polycation carrying a plurality of positive charges and an anionic polymer of this invention. In specific embodiments, a bilayer can comprise two or more different cations or polycations. In specific embodiments, a bilayer can comprise two or more different charge dynamic anionic polymers of this invention. In specific embodiments, a multiple layer polyelectrolyte film can further comprise one or more layers that do not contain a charge dynamic anionic polymer. In specific embodiments, a multiple layer polyelectrolyte film can further comprise one or more layers that contain a neutral, zwitterionic or cationic polymer which is not derived by removal of groups from a dynamic anionic polymer.

Initial studies of the formation of multilayers employing an anionic charge dynamic polymer used polymer 2 as described in the Examples.

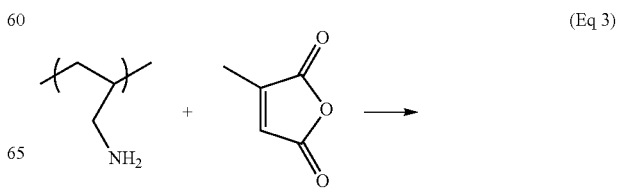

(Eq 3)

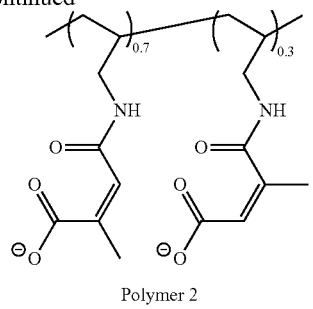

Polymer 2

The present polymers are dynamic charge state anionic polymers that have anionic charge which is a characteristic of the polymeric backbone and the functional groups attached to the polymeric backbone. Anionic charge may be distributed throughout the polymer or in portions of the polymer, for example, in certain blocks of a block copolymer. Anionic charge may be on the polymer backbone as well as in the functional groups on the polymer, some or all of the anionic functional groups may be removable. The polymers are designed such that the net charge of the dynamic charge state anionic polymer increases when one or more of the removable functional group(s), e.g., amides, is removed from the dynamic charge state anionic polymer.

Based on these criteria, the polymer backbone is not particularly limited, so long as a portion of the repeat units of the polymer have removable side chains that allow for charge shifting as defined herein, for example, amide side chains. Polymers of the invention can be prepared, for example, from a starting polymer in which a portion of the repeating units have primary amine side chains that can be converted to amides. In some embodiments, the polymer backbone is not charged. Generally speaking, the charge of the polymer is measured under conditions in which it will be used. In some cases the charge of the polymer is measured at physiological pH. In general, suitable polymeric backbones for dynamic charge state anionic polymers of the invention are any natural or synthetic polymers or copolymers having primary amine groups or which can be modified to incorporate primary amine groups. Specific examples of such suitable polymeric backbones include, among others, poly(allylamine), poly(vinylamine), branched poly(ethylene imine), poly(lysine) or more generally polypeptides which contain lysine, poly(amidoamine) dendrimers, polysaccharides having amine groups or side groups with amine groups, such as chitosan. In the present polymers, the polymeric backbone may be linear, branched or hyperbranched. Note that generally, amide groups can be introduced into polymers containing a primary amine group employing reaction with anhydrides as exemplified in equation 3 above.

The present polymer is generally anionic, but different functional groups attached to the polymer can render the polymer zwitterionic. The present polymer may also be capable of buffering changes in pH which results from the make-up of the polymer backbone and/or the attached functional groups.

Similar to the backbone, the identity of the one or more removable functional group(s) of the present polymers is not particularly limited as long as removal of the one or more removable functional group(s) decreases the anionic charge density of the polymer. As used herein, "removable functional group" means a chemical group that, upon removal, will decrease the anionic charge density of the polymer. In a specific embodiment, the functional group that is removed is a group that is not a polymer which contains a plurality of repeating units. In a specific embodiment, the removable functional group is not PEG. The functional group may, however, be an oligomer having 2 to 10 repeating units, such as a disaccharide or oligosaccharide having 2-10 monosaccharides or an oligopeptide having 2 to 10 amino acids. As will be apparent to the skilled artisan, polymers whose anionic charge decreases (i.e., becomes less anionic) in this manner can have a variety of features. For example, the removable functional group may be negatively charged so that removal of the removable functional group increases net charge. Additionally removal of the removable functional group may result in generation of a positively charged side chain further increasing net charge. One example of such a scheme is provided when the removable group contains an anionic group linked to the polymer backbone via a hydrolysable amide linkage. Other configurations that achieve the charge shifting properties of the present polymers will be apparent to those skilled in the art. When removable functional groups provide a positively charged species after removal from the polymer backbone and the backbone itself is neutral, then the present polymers can shift from being anionic to cationic when the removable functional group is removed.

In the present polymers, the mole percent of the repeat units comprising the polymeric backbone substituted with the one or more removable functional group(s) ranges from about 10 percent to about 100 percent or from 10 percent to 100 percent. In additional embodiments, the mole percent of the repeat units attached to the one or more removable functional group may range from about 30 percent to about 100 percent, from about 50 percent to about 100 percent, or from about 70 percent to about 100 percent. The polymers of the present invention may have any desired molecular weight, such as from 1,000 to 100,000 grams/mole, or from about 2,000 to 50,000 grams/mole in some embodiments.

The present dynamic charge state anionic polymers can be non-immunogenic, non-toxic or both nonimmunogenic and non-toxic. In the present polymers, polymeric backbone can be degradable or nondegradable. In some embodiments, the polymers of the invention are biodegradable and biocompatible.

The molecular weights of the polymers may range from 5,000 g/mol to over 100,000 g/mol in some embodiments and from 4,000 g/mol to 50,000 g/mol in other embodiments. In some embodiments, the polymers are relatively non-cytotoxic. In other embodiments, the polymers are biocompatible and biodegradable.

Synthesis of Polymers

The polymers of this invention may be prepared by any method known in the art. In some embodiments, the polymers are prepared from commercially available starting materials. In other embodiments, the polymers are prepared from easily and/or inexpensively prepared starting materials. Methods described herein can be employed to prepare anionic polymers of this invention.

The synthesized polymer may be purified by any technique known in the art including, but not limited to, precipitation, crystallization, chromatography, etc. In some embodiments, the polymer need not be purified. In some embodiments, the polymer is purified through repeated precipitations from an organic solvent (e.g., diethyl ether, hexane, etc.). In some embodiments, the polymer is isolated as a salt, such as a hydrochloride salt or a pharmaceutically acceptable salt. As would be appreciated by one of skill in this art, the molecular weight of the synthesized polymer and the extent of cross-linking may be determined by the reaction conditions (e.g., temperature, starting materials, concentration, order of addition, solvent, etc.) used in the synthesis (Odian Principles of Polymerization 3rd Ed., New York: John Wiley & Sons, 1991; Stevens Polymer Chemistry: An Introduction 2nd Ed., New York: Oxford University Press, 1990; each of which is incorporated herein by reference).

In one embodiment, a library of different polymers is prepared in parallel. A different amount of the one or more removable functional groups is added to each vial in a set of vials used to prepare the library. The array of vials is incubated at a temperature and length of time sufficient to allow functionalization of the polymers to occur. The polymers may then be isolated and purified using techniques known in the art. The polymers may then be screened using high-throughput techniques to identify polymers with a desired characteristic (e.g., solubility in water, solubility at different pH, ability to bind small molecules, ability to form microparticles or nanoparticles, etc.).

Interpolyelectrolyte Complexes

The present invention also provides the present polymers complexed with one or more cations thereby forming an interpolyelectrolyte complex. In the interpolyelectrolyte complexes of the present invention, the cation bound by the polymer is not particularly limited. In some embodiments, the cation need only have a single positive charge. In specific embodiments, the cation is a cation other than a metal cation. In specific embodiments, the cation is an organic species having 6-50 or 6-100 carbon atoms. In some embodiments, the cation need only have at least two positive charges. Suitable examples of cationic molecules include, among others, proteins, peptides, therapeutic molecules or agents, diagnostic molecules or agents, natural or synthetic polymers, prophylactic agents, small molecules, organometallic compounds, drugs, vaccines, immunological agents, and the like.

The cations may be naturally occurring or synthetic as synthetic polycations may also be used to form interpolyelectrolyte complexes of the invention. In some embodiments, the polymers of the invention are complexed to a cationic molecule.

The present invention also provides polyelectrolyte multilayers which can be employed, for example, for controlled release or delivery of agents, particularly therapeutic, diagnostic or prophylactic agents. In general any species that it is desired to be released or delivered can be incorporated into polyelectrolyte multilayers. In specific embodiments, the agent is cationic. In other embodiments, the agent is an agent other than a cationic agent (e.g., anionic, neutral or zwitterionic). The agent can be selected from proteins, peptides, polysaccharides, saccharides, therapeutic molecules, diagnostic molecules, prophylactic molecules, small molecules, natural polymers, synthetic polymers, organometallic compounds, drugs, vaccines, immunological agents and more specifically includes enzymes, structural proteins, receptors, soluble receptors, ion channels, pharmaceutically active proteins, cytokines, interleukins, antibodies, antibody fragments, antigens, coagulation factors, albumin, growth factors, hormones, insulin, and the like. Polyelectrolyte multilayers of this invention are formed as is known in the art having at least one layer (i.e., polyelectrolyte bilayer) that is formed using a dynamic charge state anionic polymer or copolymer of this invention.

Cationic agents or molecules can, among others, be small molecules, natural polymers or synthetic polymers. More specifically cationic agents can be proteins which may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc.

Microparticles and Nanoparticles

The polymers of the present invention may also be used to form drug delivery devices. The polymers may be used to encapsulate cationic compounds including small molecules, proteins, peptides, metals, organometallic compounds, and the like. The polymers may be used to encapsulate a mixture of cationic species with neutral, zwitterionic or anionic species. Some of the present polymers possess one or more properties that make them particularly suitable in the preparation of drug delivery devices. Such properties may include 1) the ability of the polymer to complex and protect labile agents; and 2) the ability to neutralize the charge on positively charged agents. In some embodiments, the polymers are used to coat (form one or more layers on) particles containing the agent to be delivered (the layers may also contain the same or a different agent to be delivered.) In some such embodiments, the diameter of coated microparticles ranges from 500 nm to 50 micrometers, from 1 micrometer to 20 micrometers, or from 1 micrometer to 10 micrometers. In other embodiments, the coated microparticles range from 1-5 micrometers. In other embodiments, the coated particles are less than 1 micrometer (nanoparticles). The polymers of this invention can be employed to form microcapsules or nanocapsules which may contain an agent to be delivered. The capsules are formed from polyelectrolyte multilayers in which are least one layer is formed from a dynamic charge state anionic polymer or copolymer of this invention. Capsules can be formed, for example, by initial formation of polyelectrolyte multilayers on a particle and thereafter degrading the particle. Both micro- and nanoparticles can be formed. Methods for deposition of films onto particles, are well-known in the art[53].

The polymer of this invention may be combined with other polymers (e.g., PEG, PLGA) to form the microspheres. Methods for the formation of microspheres are well-known in the art. Microparticles may be prepared using various methods. Examples of such methods include, but are not limited to, spray drying, single and double emulsion solvent evaporation, solvent extraction, phase separation, simple and complex coacervation, and other methods well known to those of ordinary skill in the art. In some embodiments, the methods for preparing the particles are the double emulsion process and spray drying methods. The conditions used in preparing the microparticles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the polymer matrix.

Methods developed for making microparticles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, J. Controlled Release 5:13-22, 1987; Mathiowitz et al. Reactive Polymers 6:275-283, 1987; Mathiowitz et ai. J. Appl. Polymer Sci. 35:755-774, 1988; each of which is incorporated herein by reference). Nanoparticles likewise can be formed by methods that are well-known in the art.

If the particles prepared by any of the above methods have a size range outside of the desired range, the particles can be sized, for example, using a sieve.

Polyelectrolyte multilayers may be formed, for example, as described in Vazquez et al., J. Am. Chem. Soc. 124, 13992 (2002). The number of layers in such multilayers is not particularly limited. Additionally, different layers of these multilayers can contain different polymers and/or anions. The present invention contemplates that these multilayer structures can be used for controlled release of a desired agent or delivery of multiple agents. As is understood by the skilled artisan, the film growth of the layered structure is primarily dictated by electrostatic interactions, hydrophobic interactions, hydrogen bonding, salt concentration, and solution pH. The polyelectrolyte multilayers can also be used to deliver cations to a selected environment, including delivery to a cell or tissue.

Agent

The agents to be delivered by the systems of the present invention may be therapeutic, diagnostic, or prophylactic agents. Any cationic chemical compound to be administered to an individual may be delivered using the interpolyelectrolyte complex. The agent may be a small molecule, natural polymer, synthetic polymer, organometallic compound, protein, peptide, polynucleotide, metal, an isotopically labeled chemical compound, drug, vaccine, immunological agent, or the like. Any chemical compound to be administered to an individual or for which controlled release or delivery is desired can be released or delivered employing polyelectrolyte multilayers of this invention.

In some embodiments, the agents are organic compounds with pharmaceutical activity. In another embodiment of the invention, the agent is a clinically used drug. In some such embodiments, the drug is an antibiotic, anti-viral agent, anesthetic, steroidal agent, anti-inflammatory agent, antineoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, or the like, or combinations thereof.

In some embodiments of the present invention, the agent to be delivered or released may be a mixture of agents. For example, a local anesthetic may be delivered or released in combination with an anti-inflammatory agent such as a steroid. Local anesthetics may also be administered with vasoactive agents such as epinephrine. As a further example, an antibiotic may be combined with an inhibitor of the enzyme commonly produced by bacteria to inactivate an antibiotic (e.g., penicillin and clavulanic acid). A neutral, zwitterionic or anionic species which may be a therapeutic, diagnostic or prophylactic agent may be delivered or released from the multilayer along with a cationic species. In specific embodiments, the cationic species employed with the charge dynamic anionic polymer of this invention to form multilayers need not itself be the agent that is to be delivered, a neutral zwitterionic or anionic species also encapsulated in the polyelectrolyte multilayer may be the agent that is to be released or delivered.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Prophylactic agents of the invention include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococcccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucel, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Targeting Agents or Ligands

The polymers and multilayer structures (e.g., coated particles and capsules) of the invention may be modified to include one or more targeting agents or ligands, since it is often desirable to target a particular cell, collection of cells, or tissue. A variety of targeting agents that direct pharmaceutical compositions to particular cells are known in the art (see, for example, Cotten et al. Methods Enzym. 217:618, 1993; incorporated herein by reference). The targeting agents may be included throughout the particle or may be only on the surface. The targeting agent may be a protein, peptide, carbohydrate, glycoprotein, lipid, small molecule, antibody, antibody fragment, receptor or the like. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferring, asialycoproteins, gp120 envelope protein of the human immunodeficiency virus (HIV), carbohydrates, receptor ligands, sialic acid, and the like. If the targeting agent is included throughout the structure, the targeting agent may be included in the mixture that is used to form the particles. If the targeting agent is only present on the surface, the targeting agent may be associated with (i.e., by covalent, hydrophobic, hydrogen boding, van der Waals, or other interactions) the formed particles using standard chemical techniques.

The amine groups on a given polymer can also be conjugated either directly to the amine groups or via spacer molecules, with targeting ligands and the like. Preferably, only a portion of the available amine groups are coupled to the ligand or spacer ligand such that the net charge of the polymer is anionic. The target ligands conjugated to the polymer direct the polymer-nucleic acid/drug complex to bind to specific target cells and penetrate into such cells (tumor cells, liver cells, heamatopoietic cells, and the like). The target ligands can also be an intracellular targeting element, enabling the transfer of the nucleic acid/drug to be guided towards certain favored cellular compartments (mitochondria, nucleus, and the like). In certain embodiments, the ligands can be sugar moieties coupled to the amino groups. Such sugar moieties are preferably mono- or oligo-saccharides, such as galactose, glucose, fucose, fructose, lactose, sucrose, mannose, cellobiose, nytrose, triose, dextrose, trehalose, maltose, galactosamine, glucosamine, galacturonic acid, glucuronic acid, and gluconic acid.

The conjugation of an acid derivative of a sugar with the polymer is preferred in some embodiments. In some such embodiments of the present invention, lactobionic acid (4-0-~-D-galactopyranosyl-D-gluconic acid) is coupled to the polymer. The galactosyl unit of lactose provides a convenient targeting molecule for hepatocyte cells because of the high affinity and avidity of the galactose receptor on these cells.

Other types of ligands that may be used include peptides such as antibodies or antibody fragments, cell receptors, growth factor receptors, cytokine receptors, transferrin, epidermal growth factor (EGF), insulin, asialoorosomucoid, mannose-6-phosphate (monocytes), mannose (macrophage, some B cells), Lewisx and sialyl Lewisx (endothelial cells), N-acetyllactosamine (T cells), galactose (colon carcinoma cells), and thrombomodulin (mouse lung endothelial cells), fusogenic agents such as polymixin B and hemaglutinin HAI, lysosomotrophic agents, nucleus localization signals (NLS) such as T-antigen, and the like.

Pharmaceutical Compositions

Once the polymer, interpolyelectrolyte complex, e.g. polymer complexed with cationic molecule or compound) or multilayer structure (coated microparticle or microcapsule) have been prepared, they may be combined with one or more pharmaceutical excipients to form a pharmaceutical composition that is suitable to administer to animals. Animals include humans as well as non-human animals, including, for example, mammals, birds, reptiles, amphibians, and fish. Preferably, the nonhuman animal is a mammal (e.g., a rodent, a mouse, a rat, a rabbit, a monkey, a dog, a cat, a primate, or a pig). An animal may be a transgenic animal. As would be appreciated by one of skill in this art, the excipients may be chosen based on the route of administration as described below, the agent being delivered, time course of delivery of the agent, or other factors.

Pharmaceutical compositions of the present invention and for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, polynucleotide/polymer complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables. In some embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the microparticles or nanoparticles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispersing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

The present invention also provides methods of administering the present polymers and complexes. Generally, these methods can involve contacting an interpolyelectrolyte complex of the present invention with one or more cells, such as those that make up a tissue. In one embodiment, the interpolyelectrolyte complex is administered to an animal. The interpolyelectrolyte complex can be administered in any suitable manner, such as in the manner and formulations described above. In some embodiments, in solution the side chain esters slowly hydrolyze, resulting in the release of the cationic component that is bound electrostatically to the polymer.

The present invention also provides methods for delivering a cationic compound to a cell or tissue. In one aspect the present methods involve contacting a composition that includes a interpolyelectrolyte complex of the invention with a target cell thereby allowing the target cell to uptake the composition. The polymer of the present invention is designed such that when the interpolyelectrolyte complex enters the target cell, one or more of the removable functional group(s) is removed from the dynamic charge state anionic polymer which increases the cationic charge density (or decreased the anionic charge density) of the dynamic charge state anionic polymer. The decrease in the anionic charge of the polymer is caused by the removal of anionic charges which promotes dissociation of the interpolyelectrolyte complex into the dynamic charge state anionic polymer and the cationic molecule, allowing for release of the cationic molecule or in particular the delivery of the cationic molecule to the target cell or cell compartment, such as an endosome, cytosol or nucleus of the cell. In some methods, at least one of the one or more of the removable functional group(s) is removed from the dynamic charge state anionic polymer in a nucleus, endosome or cytosol of the target cell. In this manner, the interpolyelectrolyte complex can dissociate primarily in the desired compartment of the target cell and deliver the cationic molecule to the target cell compartment. The present methods can also involve providing the interpolyelectrolyte complex and/or preparing the interpolyelectrolyte complex. Generally, the interpolyelectrolyte complex will be prepared by mixing the dynamic charge state anionic polymer with the cationic molecule thereby allowing formation of the interpolyelectrolyte complex.

In another aspect, the present methods involve bringing a polyelectrolyte multilayer film or coating into contact with an environment, including tissue or cells to which or into which an agent is to delivered or released. The multilayer includes at least one layer (i.e., a bilayer) comprising a charge dynamic anionic polymer of this invention and at least one cationic species and preferably comprises a plurality of such layers. The polymer of the present invention is designed such that when one or more of the removable functional group(s) is removed from the dynamic charge state anionic polymer the anionic charge of the dynamic charge state anionic polymer decreases (or the cationic charge of the polymer increases). The decrease in the anionic charge of the polymer is caused by the removal of anionic charges which promotes dissociation of polyelectrolyte layers in the multilayer allowing for release of the cationic species and/or a neutral, zwitterionic or anionic agent also comprised in the multilayer. The present methods can also involve providing the polyelectrolyte multilayer. The environment into which the agent is released can be a biological environment, which for example can be human or animal tissue.

In the present methods, the target cell or tissue can be in vitro or in vivo. Where the target cell or tissue is in vivo, the interpolyelectrolyte complex can be administered to a mammal. In some embodiments of the present methods, the cell is a eukaryotic cell.

In the present methods and polymers, removal of the one or more of the removable functional group(s) from the dynamic charge state anionic polymer can be at least partially hydrolytic, partially enzymatic and/or partially photolytic removal. The present polymers and methods can also be designed so that removal of the one or more of the removable functional groups from the dynamic charge state anionic polymer occurs at a substantially constant rate or does not occur at a constant rate. Accordingly, in the present methods, the majority, or substantially all, of the cations can be delivered to a desired environment, which may be a part of the cell, such as the nucleus, endosome or cytosol.

The present invention also provides kits for carrying out the methods described herein. Kits generally contain one or more anionic charge dynamic polymers of the invention. In one embodiment, the kit comprises instructions for carrying out any of the methods described herein. The instructions can be provided in any intelligible form through a tangible medium, such as printed on paper, computer readable media, or the like. The present kits can also include one or more reagents, buffers, media, agents and/or disposable equipment in order to readily facilitate implementation of the present methods. Examples of kit components can be found in the description above and in the following examples. Such kits may be used in hospitals, clinics, physician's offices or in patients' homes to facilitate the co-administration of the enhancing and target agents. The kits may also include as an insert printed dosing information for the co-administration of the enhancing and target agents.

These and other aspects of the present invention will be further appreciated upon consideration of the following Examples, which are intended to illustrate certain particular embodiments of the invention but are not intended to limit its scope, as defined by the claims.

DEFINITIONS

The following are terms used in the present application:

The term "alkyl" as used herein refers to saturated, straight- or branched-chain hydrocarbon radicals derived from a hydrocarbon moiety containing between one and twenty carbon atoms by removal of a single hydrogen atom. In some embodiments, alkyl groups have from 1 to 12, from 1 to 8 carbon atoms, from 1 to 6 or 1 to 3 carbon atoms. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl. A "cycloalkyl" group is a cyclic alkyl group typically containing from 3 to 8 ring members such as, but not limited to, a cyclopropyl, cyclobutyl, cyclopentyl, cyclohexyl, cycloheptyl, or cyclooctyl group.

The term "alkoxy" as used herein refers to an alkyl group, as previously defined, attached to the parent molecular moiety through an oxygen atom. Examples include, but are not limited to, methoxy, ethoxy, propoxy, isopropoxy, n-butoxy, tert-butoxy, neopentoxy, and n-hexoxy groups.

The term "alkenyl" denotes a monovalent group derived from a hydrocarbon moiety having at least one carbon-carbon double bond by the removal of a single hydrogen atom. Alkenyl groups include, for example, ethenyl, propenyl, butenyl, 1-methyl-2-buten-1-yl, and the like. Alkenyl groups include those having from 2-12 carbon atoms, those having 2-8, and those having 2-6 carbon atoms.

The term "alkynyl" as used herein refers to a monovalent group derived form a hydrocarbon having at least one carbon-carbon triple bond by the removal of a single hydrogen atom. Representative alkynyl groups include ethynyl, 2-propynyl (propargyl), 1-propynyl, and the like. Alkynyl groups include those having from 2-12 carbon atoms, those having 2-8, and those having 2-6 carbon atoms.

The term "aryl" as used herein refers to carbocyclic ring systems having at least one aromatic ring including, but not limited to, phenyl, naphthyl, tetrahydronaphthyl, indanyl, and indenyl groups, and the like. Aryl groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide. In addition, substituted aryl groups include tetrafluorophenyl and pentafluorophenyl.

The term "alkylene" refers to a diradical of a branched or unbranched saturated hydrocarbon chain, preferably having from 1 to 10 carbon atoms, including 1-6 carbon atoms, and 2-4 carbon atoms. This term is exemplified by groups such as methylene (—$CH_2$—), ethylene (—$CH_2CH_2$—), more generally —$(CH_2)_n$— where n is and integer from 1-about 20, including 1-10, 1-6 or 2, 3 or 4. Alkylene groups may be branched. Alkylene groups may be optionally substituted. Alkylene groups may have up to two non-hydrogen substituents per carbon atoms which do not interfere with removal of removable functional groups. Alkylene groups are useful as linker groups herein.

The term "alkyleneoxy" refers to an alkylene group ads described above in which one or more non-neighboring —CH—, —$CH_2$— or substituted —C— are replaced with an oxygen atoms, e.g., —$CH_2$—$CH_2$—O—$CH_2$—$CH_2$—, —O—$CH_2$—$CH_2$—, —$CHCH_3$-$\beta$-$CH_2$—$CH_2$—. The alkyleneoxy group can be branched or unbranched. The carbons of alkyleneoxy groups are optionally substituted with non-hydrogen substituents which do not interfere with removal of removable functional groups. Alkyleneoxy groups are useful as linker groups herein.

The term carbocyclic is used generally herein to refer to groups containing one or more carbon rings. The groups may be aromatic or aryl groups. Rings may contain 3-10 carbon atoms and one, two or three double bonds or a triple bond. These groups may include single rings of 3 to 8 atoms in size and bi- and tri-cyclic ring systems which may include aromatic six-membered aryl or aromatic groups fused to a non-aromatic ring.

The terms "heterocyclic" and "heterocyclyl", are used broadly herein to refer to an aromatic, partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. These heterocyclic and heterocyclyl rings and groups include those having from one to three heteroatoms independently selected from oxygen, sulfur, and nitrogen, in which the nitrogen and sulfur heteroatoms may optionally be oxidized and the nitrogen heteroatom may optionally be quaternary.

The terms "aromatic heterocyclic" or "heteroaryl" as used herein, refer to a cyclic aromatic radical having from five to 12 ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms. The term includes heteroaromatic rings fused to aryl ring or to carbocyclic rings. Examples of such aromatic heterocyclyl groups include, but are not limited to, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl groups, and the like.

Specific heterocyclic and aromatic heterocyclic groups that may be included in the compounds of the invention include: 3-methyl-4-(3-methylphenyl)piperazine, 3-methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)

piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl)piperazine, 4-(2-nitrophenyl)piperazine, 4-(2-nitrophenyl)piperazine, 4-(2-phenylethyl)piperazine, 4-(2pyridyl)piperazine, 4-(2-pyrimidinyl)piperazine, 4-(2,3-dimethylphenyl)piperazine, 4-(2,4-difluorophenyl)piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chlorotrifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine-, 6-fluoro-1,2,3,4-tetrahydro-2-methylquinoline, 1,4-diazacycloheptane, 2,3-dihydroindolyl, 3,3-dimethylpiperidine, 4,4-ethylenedioxypiperidine, 1,2,3,4-tetrahydroisoquinoline, 1,2,3,4tetrahydroquinoline, azacyclooctane, decahydroquinoline, piperazine, piperidine, pyrrolidine, thiomorpholine, and triazole.

The term "hydrocarbon", as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

The terms "substituted", whether preceded by the term "optionally" or not, and "substituent", as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may be further substituted. For example, a non limiting example is an aryl group that may be further substituted with, for example, a fluorine group at one or more position.

When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

As used herein, "biodegradable" compounds are those that, when introduced into cells, are broken down by the cellular machinery or by hydrolysis into components that the cells can either reuse or dispose of, in some cases without significant toxic effect on the cells (e.g., fewer than about 20% of the cells are killed when the components are added to cells in vitro). The components preferably do not induce inflammation or other adverse effects in vivo. In certain embodiments, the chemical reactions relied upon to break down the biodegradable compounds are uncatalyzed.

A "labile bond" is a covalent bond that is capable of being selectively broken. That is, a labile bond may be broken in the presence of other covalent bonds without the breakage of other covalent bonds. For example, a disulfide bond is capable of being broken in the presence of thiols without cleavage of any other bonds, such as carbon-carbon, carbon-oxygen, carbon-sulfur, carbon-nitrogen bonds, which may also be present in the molecule. "Labile" also means cleavable.

A "labile linkage" is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

In general, the "effective amount" of an active agent in a composition or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, etc. For example, the effective amount of micro- or nanoparticles containing an antigen to be delivered to immunize an individual is the amount that results in an immune response sufficient to prevent infection with an organism having the administered antigen.

As used herein, "peptide", means peptides of any length and includes proteins. The terms "polypeptide" and "oligopeptide" are used herein without any particular intended size limitation, unless a particular size is otherwise stated. The only limitation to the peptide or protein drug which may be utilized is one of functionality. The terms "protein" and "peptide" may be used interchangeably. Peptide may refer to an individual peptide or a collection of peptides. peptides preferably contain only natural amino acids, although non-natural amino acids (i.e., compounds that do not occur in nature but that can be incorporated into a polypeptide chain; see, for example, http://www.cco.caltech.edu/.about.dadgrpIUnnatstruct.gif, which displays structures of non-natural amino acids that have been successfully incorporated into functional ion channels) and/or amino acid analogs as are known in the art may alternatively be employed. Also, one or more of the amino acids in an peptide may be modified, for example, by the addition of a chemical entity such as a carbohydrate group, a phosphate group, a farnesyl group, an isofarnesyl group, a fatty acid group, a linker for conjugation, functionalization, or other modification, etc. In some embodiments, the modifications of the peptide lead to a more stable peptide (e.g., greater half-life in vivo). These modifications may include cyclization of the peptide, the incorporation of D-amino acids, etc. Typical of peptides that can be utilized are those selected from the group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, grarnicidines, and synthetic analogues, modifications and pharmacologically active fragments thereof, monoclonal antibodies and soluble vaccines.

As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

As used herein, "administering", and similar terms means delivering the composition to the individual being treated. In some instances the composition of the invention is capable of being circulated systemically where the composition binds to a target cell and is taken up by endocytosis. Thus, the composition is preferably administered to the individual systemically, typically by subcutaneous, intramuscular, intravenous, or intraperitoneal administration. Injectables for such use can be prepared in conventional forms, either as a liquid solution or suspension, or in a solid form that is suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

In some instances compositions, such as a polyelectrolyte, may be applied or formed on a surface from which one or more active agents are released on disruption of the layers of the multilayer. The composition can be administered by placing the surface in contact with the environment to which the agent is to be released or delivered. For example the coated surface may be placed in contact with tissue or other environment. The surface may the surface of a device, e.g., a medical device, which can be implanted in tissue or in contact with skin, for example. The type of surface is not particularly limited and may include glass, silicon, quartz, plastic, polymer, metal or ceramic, or any biocompatible surface.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, lactic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid. Anionic charge dynamic polymers, cationic species or other agents of the compositions of this invention may be in the form of pharmaceutically acceptable salts.

The Examples

General Considerations.

$^1$H and $^{13}$C nuclear magnetic resonance (NMR) spectra were recorded on Bruker AC+300 (300.135 MHz) and Varian UNITY 500 (499.896 MHz) spectrometers. Chemical shift values are given in ppm and are referenced with respect to residual protons from solvent. Silicon substrates (e.g., 0.5× 3.5 cm$^2$) used for the fabrication of multilayered films were cleaned with methylene chloride, ethanol, methanol, and deionized water, and dried under a stream of filtered compressed air. Surfaces were then activated by etching with oxygen plasma for 5 min (Plasma Etch, Carson City, Nev.) prior to film deposition. The optical thicknesses of films deposited on silicon substrates were determined using a Gaertner LSE ellipsometer (632.8 nm, incident angle=70°). Data were processed using the Gaertner Ellipsometer Measurement Program. Relative thicknesses were calculated assuming an average refractive index of 1.577 for the multilayered films. Thicknesses were determined in at least five different standardized locations on each substrate and are presented as an average (with standard deviation) for each film. All films were dried under a stream of filtered compressed air prior to measurement. The pH of buffers used for erosion and hydrolysis experiments was recorded using a pH meter and, for the preparation of deuterated buffers, is reported as pH. Fluorescence measurements of solutions used to erode multilayered films fabricated from fluorescently labeled polymers were made using a Fluoromax-3 fluorimeter (Jobin Yvon, Edison, N.J.). Film topography and surface roughness were obtained from height data imaged in tapping mode on a Nanoscope Multimode atomic force microscope (Digital Instruments, Santa Barbara, Calif.), using scan rates of 10-20 µm/s to obtain 256×256 pixel images. Silicon cantilevers with a spring constant of 40 N/m and a radius of curvature of <10 nm were used (model NSC15/NoAl, MikroMasch USA, Inc., Portland, Oreg.). For each sample, at least two different 10 µm×10 µm scans were obtained at randomly chosen points near the center of the film at each time point. Height data were flattened using a $2^{nd}$-order fit. Root-mean squared surface roughness ($R_{rms}$) was calculated over the scan area using the NanoScope® software package.

Materials.

Test grade n-type silicon wafers were purchased from Si-Tech, Inc. (Topsfield, Mass.). Poly(allylamine hydrochloride) (PAH, MW 60,000) was obtained from Alfa Aesar Organics (Ward Hill, Pa.). Citraconic anhydride and succinic anhydride were purchased from Aldrich Chemical Co. (Milwaukee, Wis.). 7-dimethylaminocoumarin-4-acetic acid, succinimidyl ester (NHS-activated coumarin) was purchased from Invitrogen (Carlsbad, Calif.). All other materials were used as received without further purification unless otherwise noted. Deionized water (18 MΩ) was used for washing steps and to prepare all polymer solutions. Solutions of cationic polymers used for dipping (20 mM with respect to the molecular weight of the polymer repeat unit) were prepared in 18 MΩ water and pH was adjusted to pH ~7 by using 1N NaOH. Solutions of anionic polymers (20 mM with respect to the molecular weight of the polymer repeat unit) were prepared in 18 MΩ water and pH was adjusted to pH ~8. All buffers and polymer solutions were filtered through a 0.2-μm membrane syringe filter prior to use unless otherwise noted.

Synthesis of Citraconic Amide-Substituted Polymer 2.

PAH (100 mg) was dissolved in 1.0 N NaOH (3 mL) and stirred overnight. Citraconic anhydride (400 μL, ~2 equivalents relative to amine functionality in PAH) was added dropwise to the PAH solution, and the reaction mixture was stirred overnight at room temperature. During the reaction, aqueous NaOH (6.0 N) was added as necessary to maintain the pH of the reaction solution above pH 8. The resulting reaction mixture was dialyzed (SpectraPor, MWCO=3500) against water (adjusted to pH >7 using NaOH) for 24 hours and lyophilized to yield the final product as a white powdery solid in near quantitative yield. The addition of citraconic anhydride to a primary amine leads to two isomers, one with a methyl group proximal to the newly generated amide bond, and one with the methyl group distal to the newly generated amide bond (see structure in text). The ratio of distal to proximal isomers formed under the conditions outlined above was determined to be ~7:3 using $^1$H NMR spectroscopy. $^1$H NMR data for the final product: (D$_2$O) δ (ppm)=1.2 (2H, br, CH$_2$CHCH$_2$NH), 1.7 (1H, br, CH$_2$CHCH$_2$NH), 1.93 (3H, s, COCHCCH$_3$COONa), 3.1 (2H, br, CH$_2$CHCH$_2$NH), 5.6 (proximal isomer, 0.3H, s, COCCH$_3$CHCOONa), 5.8 (distal isomer, 0.7H, s, COCHCCH$_3$COONa).

Synthesis of Succinic Amide-Substituted Polymer 3.

PAH (100 mg) was dissolved in 1.0 N NaOH (3 mL) and stirred overnight. Succinic anhydride (400 μg, ~2 equivalents relative to amine functionality in PAH) was added dropwise to the PAH solution, and the reaction mixture was stirred overnight at room temperature. During the reaction, aqueous NaOH (6.0 N) was added as necessary to maintain the pH of the reaction solution above pH 8. The resulting reaction mixture was dialyzed (SpectraPor, MWCO=3500) against water (adjusted to pH >7 using NaOH) for 24 hours and lyophilized to yield the final product as a white powdery solid in near quantitative yield. $^1$H NMR data for the final product: (D$_2$O) □ (ppm)=1.2 (2H, br, CH$_2$CHCH$_2$NH), 1.7 (1H, br, CH$_2$CHCH$_2$NH), 2.5 (4H, s, COCH$_2$CH$_2$COONa), 3.1 (2H, br, CH$_2$CHCH$_2$NH).

Synthesis of Coumarin-Labeled Poly(Allylamine Hydrochloride).

PAH (550 mg) was dissolved in methanol (~5 wt % in methanol) and 1 mL of a sodium methoxide solution (35 wt % in methanol) was added. The resulting reaction mixture was stirred for 4 hr at 45° C., precipitated NaCl was removed by filtration, and NHS-activated coumarin (9.5 mg, 0.5 mol % relative to the amine repeat units in PAH) was added and the reaction mixture was stirred overnight at room temperature. One equivalent of HCl was added to the reaction mixture, and the resulting reaction product was concentrated by rotary evaporation. The crude product was dissolved in water and purified by dialysis (SpectraPor, MWCO=3500) against deionized water at ambient temperature for three days. The resulting solution was lyophilized to yield a yellow solid that was used without further purification.

Characterization of Side-Chain Amide Hydrolysis.

$^1$H NMR experiments used to characterize the kinetics of side chain hydrolysis for functionalized polymers were conducted in the following general manner. Polymer (~10 mg) was dissolved in either deuterated phosphate buffer (0.6 mL, 0.5 M, pH=7.4) or deuterated acetate buffer (0.6 mL, 0.5 M, pH=5). 3-(trimethylsilyl)-1-propanesulfonic acid sodium salt (~3 mg) was added as an internal standard, and the resulting solution was placed in a glass NMR tube. The NMR tube was kept in a 37° C. incubator and removed periodically for analysis by $^1$H NMR spectroscopy. The disappearance of the α-proton of the side chains at 5.6 and 5.8 ppm was monitored and integrated versus the trimethylsilyl protons of the internal standard.

Fabrication of Multilayered Films.

Multilayered films were fabricated on planar silicon substrates using an alternate dipping procedure according to the following general protocol: (1) Substrates were submerged in a solution of polycation for 5 min, (2) substrates were removed and immersed in an initial water bath for 1 min followed by a second water bath for 1 min, (3) substrates were submerged in a solution of polyanion for 5 min, and (4) substrates were rinsed in the manner described above. This cycle was repeated until the desired number of polycation/polyanion bilayers (typically 20) had been deposited. For experiments designed to characterize film growth profiles by ellipsometry, films were dried after every five cycles of the above procedure using filtered compressed air. Films to be used in erosion and release experiments were either used immediately after fabrication or dried under a stream of filtered compressed air and stored in a vacuum desiccator until use. All films were fabricated at ambient room temperature.

Characterization of Film Erosion and Release Kinetics.

Experiments designed to investigate film erosion and release kinetics were performed in the following general manner: Film-coated substrates were placed in a plastic UV-transparent cuvette, and either 1.0 mL of HEPES buffer (pH=7.4) or 1.0 mL of acetate buffer (pH=5.0) was added to cover completely the film-coated portion of the substrates. These samples were incubated at 37° C. and removed at predetermined intervals for characterization by ellipsometry. Films were rinsed under deionized water and dried under a stream of filtered compressed air prior to measurement. Values of optical film thickness were determined in at least five different predetermined locations on the substrate by ellipsometry and the samples were returned immediately to the buffer solution. For experiments designed to monitor the concentrations of fluorescently labeled PAH released into solution, fluorescence measurements were made using the solution used to incubate the sample (excitation wavelength=376 nm; emission wavelength=470 nm).

Citraconic amide-functionalized polymer 2 was synthesized by the ring-opening addition of citraconic anhydride to PAH in analogy to methods described previously for the functionalization of small-molecule amines and polyamines.[30-36] Treatment of PAH with an excess of citraconic anhydride in an aqueous NaOH solution at room temperature resulted in exhaustive functionalization with citraconic amide-functionalized side chains, as determined by $^1$H NMR spectroscopy (Eq 3). The addition of citraconic anhydride to a primary amine can lead to the generation of two isomers, one with a methyl group distal to the newly generated amide bond, and one with the methyl group proximal to the newly generated amide bond (e.g., see Eq 3). The ratio of distal to proximal side chain isomers in

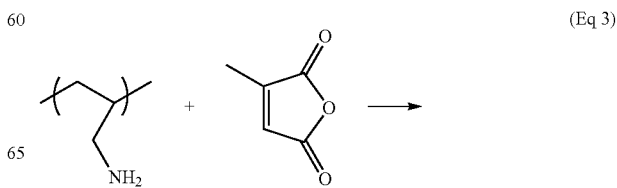

(Eq 3)

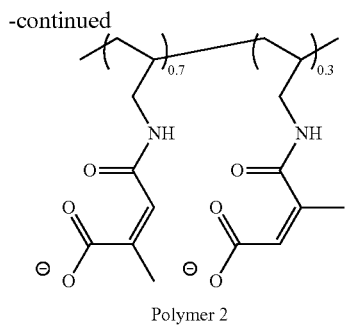

Polymer 2 samples of polymer 2 used in this study was determined to be ~7:3 by integration of the α-protons of the side chains using $^1$H NMR spectroscopy. Polymer 2 was isolated as a solid in near quantitative yield and was soluble in aqueous buffers at all concentrations required for subsequent experiments described below.

Figure 2:
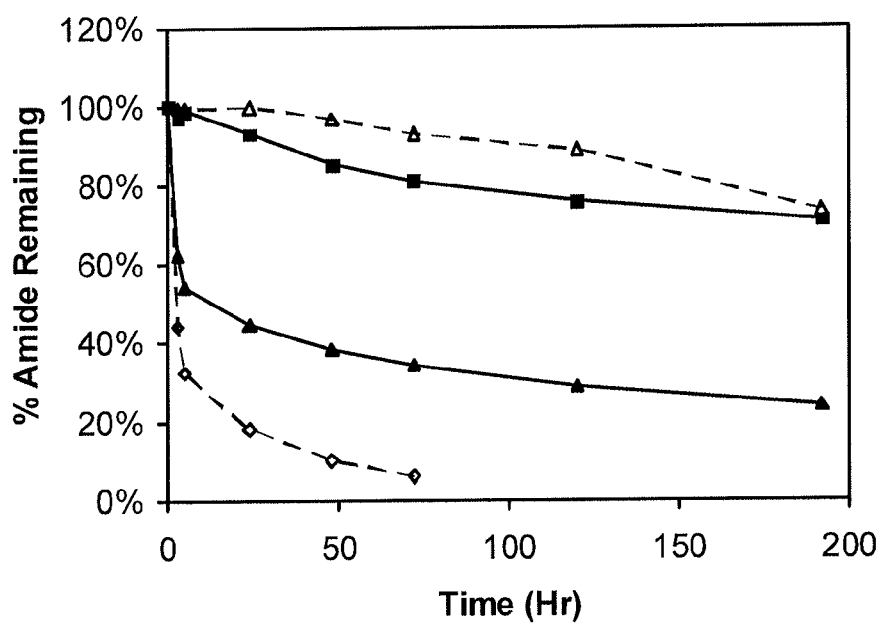
FIG. 2: Kinetics of side chain amide hydrolysis at 37° C. for polymer 2 in deuterated phosphate buffer (500 mM, pH=7.4, ■) and acetate buffer (500 mM, pH=5.0, ▲), respectively, as determined by $^1$H NMR spectroscopy. Data depicted with dashed lines correspond to the kinetics of the proximal (Δ) and distal (◇) side chain isomers of polymer 2 at pH 5.0.

As described above, past studies report that citraconic amides are relatively stable in alkaline media, but they hydrolyze readily in acidic media.30-35 Characterization of the kinetics of hydrolysis of the side chains of polymer 2 upon incubation in deuterated phosphate buffer (pH=7.4) at 37° C. using $^1$H NMR spectroscopy demonstrated that side chain hydrolysis occurred slowly at near-neutral pH. As shown in FIG. 2 (closed squares), only ~25% of the side chains of polymer 2 were hydrolyzed after incubation in phosphate buffer for eight days. However, the side chains of polymer 2 were hydrolyzed rapidly when the polymer was incubated at lower pH. For example, as shown in FIG. 2 (closed triangles), ~55% of side chains were hydrolyzed within the first five hours when polymer 2 was incubated in deuterated acetate buffer (pH=5.0). These pH-dependent results are consistent with the results of past studies.30-35

The addition of citraconic anhydride to poly(allylamine) results in the formation of two side chain isomers (see Eq 2). Further inspection of the data in FIG. 2 reveals that the rate of hydrolysis of the side chains of polymer 2 that have the methyl group distal to the amide bond is significantly greater than the rate of hydrolysis of the side chains having the methyl group proximal to the amide bond (FIG. 2, dashed lines; individual data for hydrolysis at pH 7.4 not shown). Hydrolysis of the distal isomer occurs very rapidly (e.g., ~70% conversion; open diamonds) within the first five hours and is >95% complete after 70 hours. By contrast, hydrolysis of the proximal isomer occurs much more slowly, and is only ~20% complete after incubation for eight days. These large differences in rate are consistent with the results of past studies reporting the significant influence of substituent effects on the hydrolysis of amides formed using α-methyl derivatives of maleic anhydride. In the context of this current investigation, these results, when combined, demonstrate that polymer 2 is converted over a period of several days to a polymer that contains a majority of side chains that are cationic (i.e., primary amines, with the remainder being citraconic amide proximal isomers that continue to hydrolyze more slowly) upon incubation in acidic media. In general, the actual net charge of polymer 2 would depend upon a number of different factors, including the extent of side chain hydrolysis as well as environmental factors such as solution pH and ionic strength (the relative net charges and extents of reaction depicted in FIG. 1 are indicated for illustrative purposes only).

Fabrication and Characterization of Polyelectrolyte Multilayers Fabricated Using Polymer 2.

A series of experiments was performed to determine whether polymer 2 could be used to fabricate polyelectrolyte multilayers using PAH and an alternate dipping procedure similar to that used in numerous past studies.[1-4] For these and all subsequent experiments described below, multilayered films were fabricated layer-by-layer directly on the surfaces of planar silicon substrates to facilitate the characterization of film growth and increases or decreases in film thickness using ellipsometry.

Figure 3:
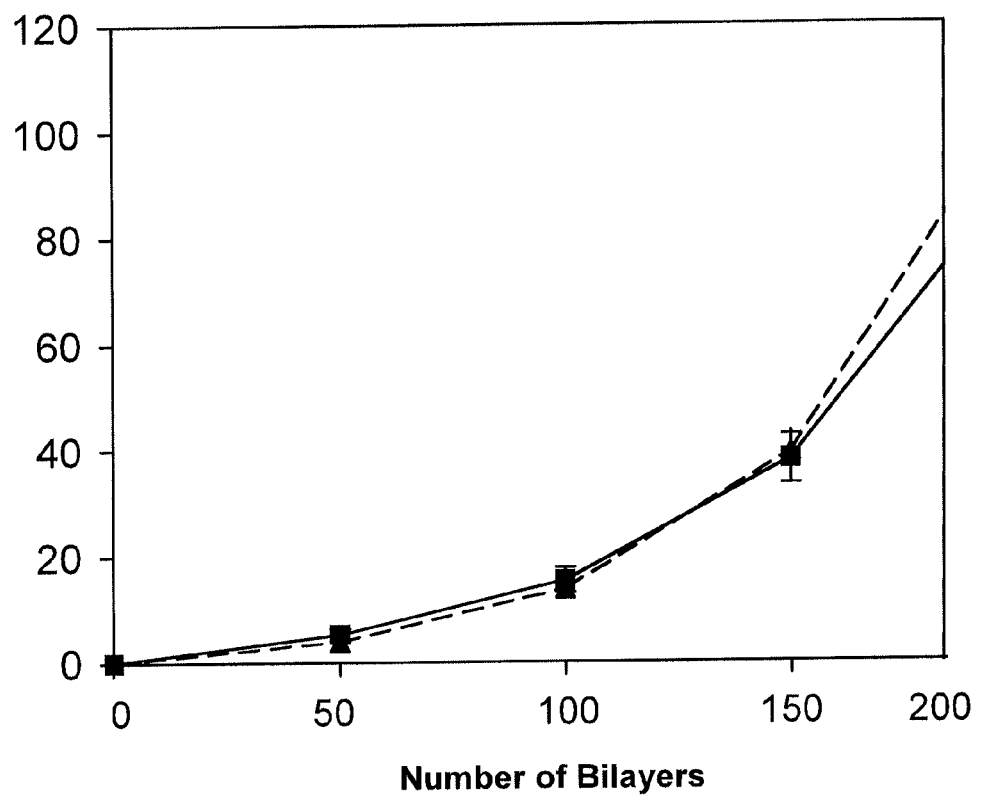
FIG. 3: Plot of ellipsometric thickness versus the number of PAH/polymer 2 bilayers (■, solid lines) or PAH/polymer 3 bilayers (▲, dashed lines) deposited on bare silicon substrates.

FIG. 3 shows a plot of optical film thickness versus the number of PAH/polymer 2 layer pairs (referred to hereafter as bilayers') deposited. Inspection of these data (filled squares) reveals an average final film thickness of ~90 nm after the deposition of 20 bilayers. Film thickness increased in a manner that was supra-linear, rather than linear, with respect to the number of bilayers deposited. This film growth behavior is similar to that reported recently for the 'exponential' growth of polyelectrolyte multilayers fabricated from a variety of different weak polycation/polyanion pairs,[40-45] and could result from the ability of one or both polyelectrolytes to diffuse within these films during assembly.[40] Characterization of the surface of a film 20 bilayers thick using atomic force microscopy revealed these films to be continuous with a root-mean squared ($R_{rms}$) surface roughness of ~13 nm.

Time-dependent hydrolysis of the amide functionality in the side chains of anionic polymers of this invention, particularly polymer 2 [which, ultimately, results in the conversion of the anionic polymer to a cationic poly(amine)] can be used to (i) change the nature of the electrostatic interactions in multilayered assemblies, and (ii) promote film disruption and disassembly in ways that can be used to provide control over the release of cationic film components.

To demonstrate this, a series of experiments were performed using films fabricated from polymer 2 and PAH labeled with a fluorescent coumarin derivative ($PAH_{FL}$). $PAH_{FL}$ was used in these experiments to facilitate characterization of the time-dependent release of PAH from films incubated in aqueous environments (described below). The growth profiles of films fabricated using polymer 2 and $PAH_{FL}$ did not vary significantly from the growth profile shown in FIG. 3 using polymer 2 and unlabeled PAH (as determined by ellipsometry, data not shown).

Figure 4:
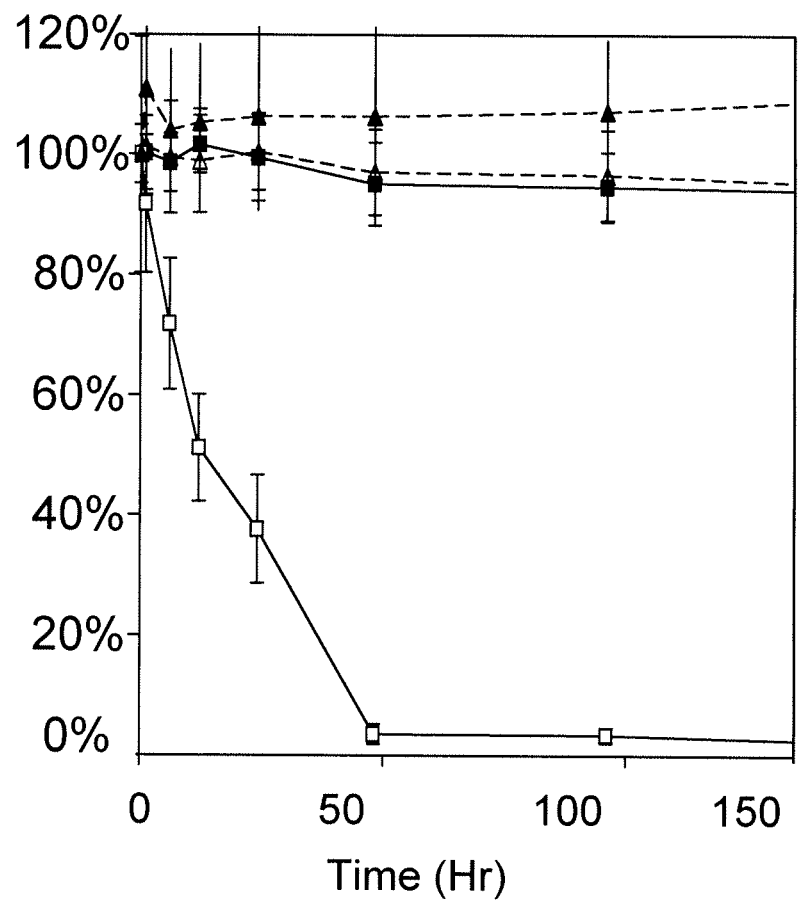
FIG. 4: Plot of film erosion versus time for multilayered films fabricated from fluorescently labelled PAH and polymer 2 (solid lines) incubated at 37° C. at pH 7.4 (■) and pH 5.0 (□). This plot also includes erosion profiles for films fabricated from polymer 3 (dashed lines) incubated at 37° C. at pH 7.4 (▲) and pH 5.0 (Δ). Film thicknesses were determined using ellipsometry at each time point and are expressed as percentages of the original thicknesses of each film.

The stability (or instability) of films fabricated from polymer 2 and $PAH_{FL}$ in near-neutral or acidic media was investigated by incubating these assemblies in HEPES buffer (pH=7.4) or acetate buffer (pH=5.0) at 37° C. FIG. 4 shows a plot of decreases in optical film thickness as a function of time measured during the incubation of films fabricated from 20 bilayers of polymer 2 and $PAH_{FL}$ (~90 nm thick). Inspection of these data reveals these films to be stable (that is, they do not decrease significantly in optical thickness) upon incubation at pH 7.4 for approximately seven days (closed squares), but that these films decrease in thickness completely, and with a profile that is essentially linear, over a period of 48 hours when incubated at pH 5.0 (open squares).

The large, pH-dependent differences in the stability and erosion profiles of the $PAH_{FL}$/polymer 2 films shown in FIG. 4 are consistent with the large and pH-dependent differences in the relative rates of solution-phase amide side chain hydrolysis shown in FIG. 2. These observations, when combined, provide general support for the view that polymer 2 destabilizez multilayers and promotes film disassembly through a time-dependent 'charge-shifting' mechanism that involves polymer side-chain hydrolysis.

The erosion of these materials at pH 5.0 could also arise from other factors, such as changes in the percent ionization of polymer 2 that could occur when these films are incubated in acidic environments. Several past studies have demonstrated, for example, that polyelectrolyte multilayers fabricated from weak polyacids [e.g., poly(acrylic acid), poly(methacrylic acid), etc.] can be dissolved and 'erased'[46-50] or transformed physically in other ways[51,52] when exposed to changes in pH that change the ionic character of the polymers and disrupt interpolyelectrolyte interactions (e.g., by protonation or deprotonation of anionic carboxylate functionality). In general, past reports describing film dissolution in multilayers fabricated using weak polyelectrolytes describe transformations that often occur very rapidly (e.g., on the order of minutes),[46,49-52] rather than over the period of ~2 days as observed in our experiments.

To provide additional support for the charge-shifting hypothesis, an additional series of experiments were conducted using films fabricated from PAH and succinic amide-functionalized polymer 3. Polymer 3 is an analog of polymer 2 synthesized by the ring-opening addition of succinic anhydride to PAH (Eq 4). Polymer 3 is particularly useful as a control in these experiments for several reasons: (i) because succinic anhydride does not contain the double bond functionality present in citraconic anhydride, succinic amides are more conformationally flexible than citraconic amides, (ii) the terminal carboxylate functionality of succinic amides is thus not maintained in close proximity to the amide group, and, as a result (iii) rates of hydrolysis of succinic amides are much slower than the corresponding rates of hydrolysis of citraconic amides.[33]

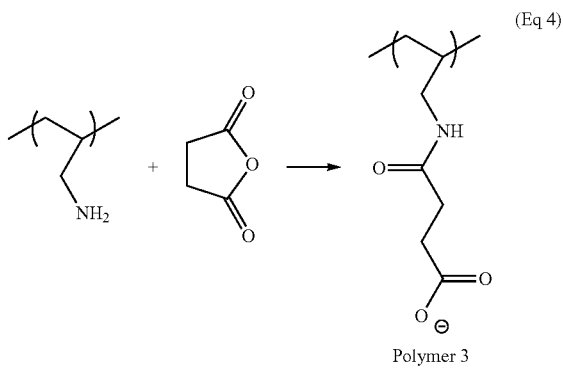

(Eq 4)

Polymer 3

FIG. 3 (dashed line) shows a plot of film thickness for a PAH/polymer 3 film versus the number of bilayers of polymer 3 and PAH deposited, and demonstrates that the conformational flexibility of the polymer side chain does not influence film growth significantly relative to films fabricated from polymer 2. However, striking differences in the stability of films fabricated from polymer 3 were observed when these films were incubated in aqueous media. Inspection of the data in FIG. 3 (dashed lines) reveals that films fabricated from polymer 3 are stable and do not decrease in optical thickness for up to seven days upon incubation at either pH 7.4 or pH 5.0. These results provide additional strong support for the view that the erosion of films fabricated from polymer 2 occurs as a result of the hydrolysis of the side chains in polymer 2 (and a concomitant change in the net charge of the polymer), and not as a result of other factors (such as changes in pH, ionic strength, or the percent ionization of the polymer) that could occur during the incubation of these films in acidic environments.

The gradual erosion of films fabricated from polymer 2 and $PAH_{FL}$ in acidic environments results in the gradual and controlled release of $PAH_{FL}$ into solution. FIG. 4 shows a plot of solution fluorescence intensity versus time measured during the film incubation and erosion experiments described above in FIG. 3. Inspection of these data reveals that $PAH_{FL}$ was released gradually into solution for up to ~100 hours (open squares) when films fabricated from polymer 2 were incubated at pH 5.0. By contrast, levels of solution fluorescence observed during the incubation of these films at pH 7.4 (closed squares) were very low over the entire course of the experiment.

Figure 5:
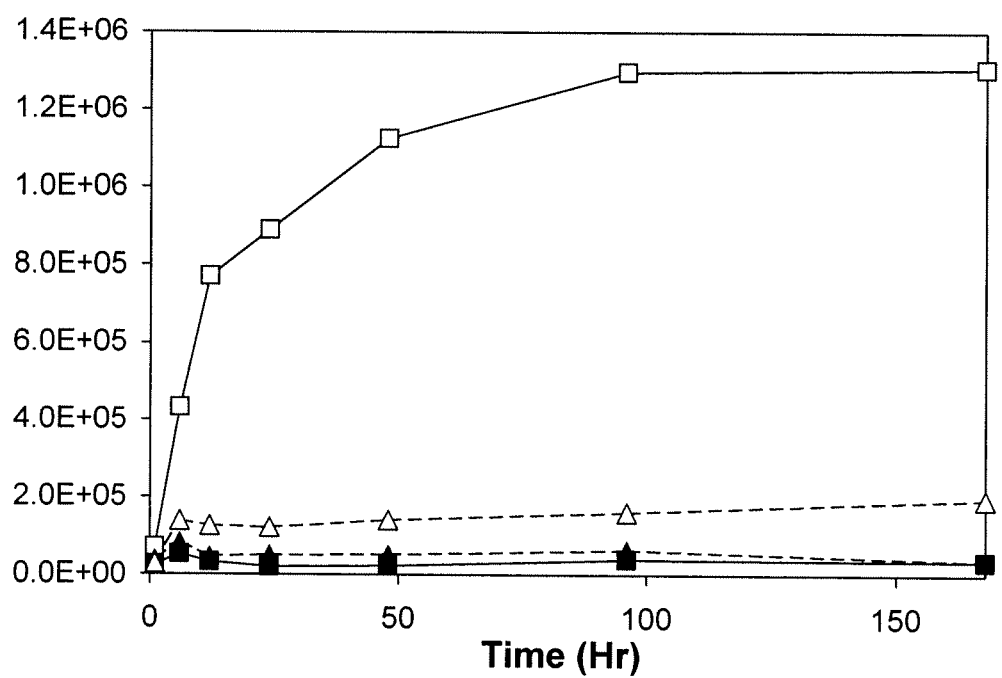
FIG. 5: Plot of coumarin fluorescence versus time showing the release of coumarin labeled PAH from multilayered films fabricated from using polymer 2 (solid lines) incubated at 37° C. at pH 7.4 (■) and pH 5.0 (□). This plot also includes release profiles for films fabricated from polymer 3 (dashed lines) incubated at 37° C. at pH 7.4 (▲) and pH 5.0 (Δ).

These data are consistent with the pH-dependent results of film erosion discussed above and demonstrate that polymer 2 can be used to design polyelectrolyte multilayers that are stable at neutral or near-neutral pH, but permit control over the surface-mediated release of a cationic agent for approximately four days under acidic conditions. On the basis of these solution fluorescence measurements, it is estimated that films 20 bilayers thick contained approximately 20 μg of $PAH_{FL}$ per cm². Because layer-by-layer assembly can be used to exert precise control over film thickness and, thus, the amount of PAH incorporated (e.g., by controlling the number of layers of polymer deposited), this general approach can be used to increase (or decrease) the amounts of PAH or other functional cationic agents incorporated into and released from these materials. Finally, the remaining data in FIG. 5 (dashed lines) correspond to cumulative amounts of solution fluorescence measured during the incubation of control films fabricated from $PAH_{FL}$ and polymer 3. These data demonstrate that these films do not release significant amounts of $PAH_{FL}$ and are consistent with the results of the erosion experiments described above.

The use of 'charge-shifting' anionic polymers provides control over the disruption of ultrathin multilayered polyelectrolyte films in aqueous environments. The addition of certain anhydrides to poly(alkeneamine), and particularly the use of citraconic anhydride to poly(allylamine), a commercially-available polyamine used widely to fabricate polyelectrolyte multilayers, yields an anionic, carboxylate-functionalized polymer (e.g., polymer 2) that can be converted readily back to cationic poly(alkeneamine) in acidic environments (e.g., pH 5). The incorporation of such polymers, e.g., polymer 2, as an anionic component in polyelectrolyte multilayers provides an approach to the fabrication of films that are relatively stable at neutral pH (e.g., pH ~7) but that erode over a period of time, in some cases over several days, when exposed to low pH environments (e.g., pH ~5). Control experiments using a structural analog of polymer 2 functionalized with carboxylate side chains that do not hydrolyze as readily as those of polymer 2 provided support that the disruption of these films occurred as a result of polymer side chain hydrolysis (and a resulting change in the net charge of the polymer) and not as a result of other factors, such as changes in pH or ionic strength, that could occur upon the incubation of these assemblies. These results also indicate that the rate of disruption of such multilayer films can be controlled by selection of the amide groups attached to the polymer backbone. For example, the relative amounts of amide side chains having double bonds and those not having double bonds can be varied to vary the rate and extent of side chain hydrolysis and the rate and extent of film disruption.

Because the method of this invention is based upon the use of anionic polymers to induce film instability, it provides a platform for the design of polyelectrolyte multilayers that can be used to provide control over the release of cationic film components. In a specific embodiment, ultrathin films (e.g., ~100 nm thick) fabricated using polymer 2 sustain the release of fluorescently labeled PAH for up to four days when incubated at pH 5.0.

The work described here differs fundamentally from approaches that have been reported previously for the disruption of polyelectrolyte multilayers using degradable cationic polymers, significantly expands the range of different cationic agents (e.g., cationic proteins, peptides, polymers, nanoparticles, etc.) that can be released or delivered from surfaces using polyelectrolyte multilayers.

In addition, the synthetic approach used here is modular and can be used to introduce anionic 'charge-shifting' character to a broad range of other primary amine-functionalized polymers. The method of this invention can be used to tune the 'charge-shifting' character of these polymers over a broad range of times, and for a broad range of potential applications, by varying either the numbers or the structures of the 'charge-shifting' anionic side chains incorporated. The relative instability of these materials at pH values representative of those found in the endosomes and lysosomes of cells also suggests opportunities to design film-coated particles or hollow multilayer microcapsules designed for the intracellular delivery of therapeutic macromolecules.[53]

The present methods may be carried out by performing any of the steps described herein, either alone or in various combinations. The present compounds may also have any or all of the components described herein. One skilled in the art will recognize that all embodiments of the present invention are capable of use with all other embodiments of the invention described herein. Additionally, one skilled in the art will realize that the present invention also encompasses variations of the present methods and compositions that specifically exclude one or more of the steps, components or groups described herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

Accordingly, for all purposes, the present invention encompasses not only the main group, but also the main group absent one or more of the group members. The present invention also envisages the explicit exclusion of one or more of any of the group members in the claimed invention.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. Accordingly, for all purposes, the present invention encompasses not only the main group, but also the main group absent one or more of the group members. The present invention also envisages the explicit exclusion of one or more of any of the group members in the claimed invention.

Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt. Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The broad term comprising is intended to encompass the narrower consisting essentially of and the even narrower consisting of: Thus, in any recitation herein of a phrase "comprising one or more claim element" (e.g., "comprising A and B"), the phrase is intended to encompass the narrower, for example, "consisting essentially of A and B" and "consisting of A and B." Thus, the broader word "comprising" is intended to provide specific support in each use herein for either "consisting essentially of" or "consisting of." The invention illustratively described herein suitably may be practiced in the absence of any element or elements, limitation or limitations which is not specifically disclosed herein.

One of ordinary skill in the art will appreciate that starting materials, catalysts, reagents, synthetic methods, purification methods, analytical methods, and assay methods, other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials; alternative starting materials, reagents, methods of synthesis, purification methods, and methods of analysis; as well as additional uses of the invention.

Unless otherwise specified, "a" or "an" means "one or more".

While certain specific embodiments have been illustrated and described, it should be understood that changes and modifications can be made therein in accordance with ordinary skill in the art without departing from the invention in its broader aspects as defined in the following claims.

REFERENCES

1 G. Decher, *Science*, 1997, 277, 1232.
2 P. Bertrand, A. Jonas, A. Laschewsky, and R. Legras, *Macromol Rapid Comm*, 2000, 21, 319.
3 C. S. Peyratout and L. Dahne, *Angew Chem Int Edit*, 2004, 43, 3762.
4 P. T. Hammond, *Adv Mater*, 2004, 16, 1271.
5 H. Ai, S. A. Jones, and Y. M. Lvov, *Cell Biochem Biophys*, 2003, 39, 23.
6 S. A. Sukhishvili, *Curr Opin Colloid In*, 2005, 10, 37.
7 Z. Y. Tang, Y. Wang, P. Podsiadlo, and N. A. Kotov, *Adv Mater*, 2006, 18, 3203.
8 D. M. Lynn, *Soft Matter*, 2006, 2, 269.
9 B. G. De Geest, N. N. Sanders, G. B. Sukhorukov, J. Demeester, and S. C. De Smedt, *Chem Soc Rev*, 2007, 36, 636.
10 D. M. Lynn, *Adv Mater*, 2007, 19, 4118.
11 J. Zhang, L. S. Chua, and D. M. Lynn, *Langmuir*, 2004, 20, 8015.
12 K. C. Wood, J. Q. Boedicker, D. M. Lynn, and P. T. Hammond, *Langmuir*, 2005, 21, 1603.
13 J. Zhang, N. J. Fredin, J. F. Janz, B. Sun, and D. M. Lynn, *Langmuir*, 2006, 22, 239.
14 J. Zhang and D. M. Lynn, *Macromolecules*, 2006, 39, 8928.
15 K. C. Wood, H. F. Chuang, R. D. Batten, D. M. Lynn, and P. T. Hammond, *Proc Natl Acad Sci USA*, 2006, 103, 10207.
16 J. T. Zhang, S. I. Montanez, C. M. Jewell, and D. M. Lynn, *Langmuir*, 2007, 23, 11139.
17 C. Picart, A. Schneider, O. Etienne, J. Mutterer, P. Schaaf, C. Egles, N. Jessel, and J. C. Voegel, *Adv Funct Mater*, 2005, 15, 1771.
18 K. F. Ren, J. Ji, and J. C. Shen, *Biomaterials*, 2006, 27, 1152.
19 N. Jessel, M. Oulad-Abdelghani, F. Meyer, P. Lavalle, Y. Haikel, P. Schaaf, and J. C. Voegel, *Proc Natl Acad Sci USA*, 2006, 103, 8618.
20 J. Blacklock, H. Handa, D. Soundara Manickam, G. Mao, A. Mukhopadhyay, and D. Oupicky, *Biomaterials*, 2007, 28, 117.
21 J. Chen, S. Huang, W. Lin, and R. Zhuo, *Small*, 2007, 3, 636.
22 T. Serizawa, M. Yamaguchi, and M. Akashi, *Angew Chem Int Edit*, 2003, 42, 1115.
23 O. Etienne, A. Schneider, C. Taddei, L. Richert, P. Schaaf, J. C. Voegel, C. Egles, and C. Picart, *Biomacromolecules*, 2005, 6, 726.
24 J. T. Zhang and D. M. Lynn, *Adv Mater*, 2007, 19, 4218.
25 A. M. Funhoff, C. F. van Nostrum, A. P. C. A. Janssen, M. H. A. Fens, D. J. A. Crommelin, and W. E. Hennink, *Pharm Res*, 2004, 21, 170.
26 B. G. De Geest, R. E. Vandenbroucke, A. M. Guenther, G. B. Sukhorukov, W. E. Hennink, N. N. Sanders, J. Demeester, and S. C. De Smedt, *Adv Mater*, 2006, 18, 1005.
27 J. Luten, N. Akeroyd, A. Funhoff, M. C. Lok, H. Talsma, and W. E. Hennink, *Bioconjugate Chem*, 2006, 17, 1077.
28 X. Jiang, M. C. Lok, and W. E. Hennink, *Bioconjugate Chem*, 2007, 18, 2077.
29 M. S. Shim and Y. J. Kwon, *Biomacromolecules*, 2008, 9, 444.
30 A. J. Kirby and P. W. Lancaster, *J Chem Soc Perk T 2*, 1972, 1206.
31 M. F. Aldersle, A. J. Kirby, P. W. Lancaster, R. S. Mcdonald, and C. R. Smith, *J Chem Soc Perk T 2*, 1974, 1487.
32 D. B. Rozema, K. Ekena, D. L. Lewis, A. G. Loomis, and J. A. Wolff, *Bioconjugate Chem*, 2003, 14, 51.
33 Y. Lee, S. Fukushima, Y. Bae, S. Hiki, T. Ishii, and K. Kataoka, *J Am Chem Soc*, 2007, 129, 5362.

34 M. Meyer, A. Zintchenko, M. Ogris, and E. Wagner, *J Gene Med,* 2007, 9, 797.

35 D. B. Rozema, D. L. Lewis, D. H. Wakefield, S. C. Wong, J. J. Klein, P. L. Roesch, S. L. Bertin, T. W. Reppen, Q. Chu, A. V. Blokhin, J. E. Hagstrom, and J. A. Wolff, *Proc Natl Acad Sci USA,* 2007, 104, 12982.

36 P. S. Xu, E. A. Van Kirk, Y. H. Zhan, W. J. Murdoch, M. Radosz, and Y. Q. Shen, *Angew Chem Int Edit,* 2007, 46, 4999.

37 H. B. F. Dixon and R. N. Perham, *Biochem J,* 1968, 109, 312.

38 J. K. Shetty and J. E. Kinsella, *Biochem J,* 1980, 191, 269.

39 J. G. Bindels, L. W. Misdom, and H. J. Hoenders, *Biochim Biophys Acta,* 1985, 828, 255.

40 C. Picart, J. Mutterer, L. Richert, Y. Luo, G. D. Prestwich, P. Schaaf, J. C. Voegel, and P. Lavalle, *Proc Natl Acad Sci USA,* 2002, 99, 12531.

41 F. Boulmedais, V. Ball, P. Schwinte, B. Frisch, P. Schaaf, and J. C. Voegel, *Langmuir,* 2003, 19, 440.

42 B. Schoeler, E. Poptoschev, and F. Caruso, *Macromolecules,* 2003, 36, 5258.

43 P. Lavalle, V. Vivet, N. Jessel, G. Decher, J. C. Voegel, P. J. Mesini, and P. Schaaf, *Macromolecules,* 2004, 37, 1159.

44 L. Richert, P. Lavalle, E. Payan, X. Z. Shu, G. D. Prestwich, J. F. Stoltz, P. Schaaf, J. C. Voegel, and C. Picart, *Langmuir,* 2004, 20, 448.

45 B. Sun, C. M. Jewell, N. J. Fredin, and D. M. Lynn, *Langmuir,* 2007, 23, 8452.

46 S. A. Sukhishvili and S. Granick, *J Am Chem Soc,* 2000, 122, 9550.

47 S. T. Dubas, T. R. Farhat, and J. B. Schlenoff, *J Am Chem Soc,* 2001, 123, 5368.

48 S. T. Dubas and J. B. Schlenoff, *Macromolecules,* 2001, 34, 3736.

49 S. A. Sukhishvili and S. Granick, *Macromolecules,* 2002, 35, 301.

50 J. Cho and F. Caruso, *Macromolecules,* 2003, 36, 2845.

51 J. Hiller, J. D. Mendelsohn, and M. F. Rubner, *Nat Mater,* 2002, 1, 59.

52 J. D. Mendelsohn, C. J. Barrett, V. V. Chan, A. J. Pal, A. M. Mayes, and M. F. Rubner, *Langmuir,* 2000, 16, 5017.

53. C. S. Peyratout, L. Dahne, Angew Chem Int Ed Engl, 2004, 43, 3762-83.

We claim:

1. A composition comprising one or more cations and an anionic polymer, wherein an interpolyelectrolyte complex is formed between the anionic polymer and the one or more cations and wherein the anionic polymer comprises a polymeric backbone formed from repeat units, and one or more removable functional groups attached to the polymeric backbone and distributed throughout the anionic polymer, and has an anionic charge density which decreases when one or more of the removable functional groups is removed from the anionic polymer and wherein the anionic polymer is a polymer other than poly(lysine).

2. The composition of claim 1 wherein the cations are selected from a protein, a peptide, a small molecule, a natural polymer or a synthetic polymer.

3. A composition of claim 1 further comprising one or more neutral, zwitterionic, anionic, or cationic therapeutic, diagnostic or prophylactic agents.

4. The composition of claim 1, wherein the anionic polymer has the formula:

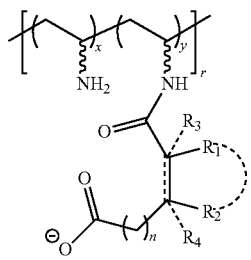

where r is an integer ranging from 5 to 100,000, x and y are numbers representing the mole percent of the indicated side chains in the polymer where x+y is 1 and y represents from 10 to 100 mole percent of amide side chain, and wherein x can be zero, the wavy line represents a linker which covalently attaches the primary amine or the amide to the polymer backbone, n is 0 or 1, dotted lines indicate optional bonds, if $R_3$ and $R_4$ are absent the bond in the ring is a double bond; and where $R_1$, $R_2$, and $R_3$ and $R_4$ are selected from optionally substituted alkyl, alkenyl, alkynyl, aryl, heteroaryl, carbocyclic and heterocyclic groups and wherein $R_1$ and $R_2$ can together form an optionally substituted 5-10 member carbocyclic or heterocyclic ring which may be aryl or heteroaryl or which can contain one or two double bonds, where optional substituents include one or more halogen, hydroxyl, alkyl, alkenyl, alkynyl, aryl, heteroaryl, carbocyclic or heterocyclic groups —CN, alkoxyl, —COOH (or —COO$^-$), —COOR, or —CON(R')$_2$, where R is alkyl, alkenyl, alkynyl, aryl, heteroaryl, carbocyclic or heterocyclic and each R' is hydrogen or R.

5. A polyelectrolyte multilayer wherein at least one layer comprises an anionic polymer and a cation, wherein the anionic polymer comprises a polymeric backbone formed from repeat units, and one or more removable functional groups attached to the polymeric backbone and distributed throughout the anionic polymer, and has an anionic charge density which decreases when one or more of the removable functional groups is removed from the anionic polymer and wherein the anionic polymer is a polymer other than poly (lysine).

6. The polyelectrolyte multilayer of claim 5, wherein the one or more removable functional groups of the anionic polymer are anionic.

7. The polyelectrolyte multilayer of claim 5, wherein the one or more removable anionic functional groups are linked to the polymer backbone by an amide linkage.

8. The polyelectrolyte multilayer of claim 5, wherein the anionic polymer has the formula:

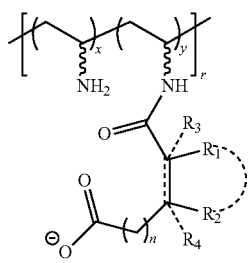

where r is an integer ranging from 5 to 100,000, x and y are numbers representing the mole percent of the indicated side chains in the polymer where x+y is 1 and y represents from 10 to 100 mole percent of amide side chain, and wherein x can be zero, the wavy line represents a linker which covalently attaches the primary amine or the amide to the polymer backbone, n is 0 or 1, dotted lines indicate optional bonds, if $R_3$ and $R_4$ are absent the bond in the ring is a double bond; and where $R_1$, $R_2$, and $R_3$ and $R_4$ are selected from optionally substituted alkyl, alkenyl, alkynyl, aryl, heteroaryl, carbocyclic and heterocyclic groups and wherein $R_1$ and $R_2$ can together form an optionally substituted 5-10 member carbocyclic or heterocyclic ring which may be aryl or heteroaryl or which can contain one or two double bonds, where optional substituents include one or more halogen, hydroxyl, alkyl, alkenyl, alkynyl, aryl, heteroaryl, carbocyclic or heterocyclic groups —CN, alkoxyl, —COOH (or —COO⁻), —COOR, or —CON(R')$_2$, where R is alkyl, alkenyl, alkynyl, aryl, heteroaryl, carbocyclic or heterocyclic and each R' is hydrogen or R.

9. The polyelectrolyte multilayer of claim 8, wherein the linker to the polymer backbone is an alkylene or alkyleneoxy linker.

10. The polyelectrolyte multilayer of claim 8, wherein the polymer contains two or more different amide side chains, where any of the variables $R_1$-$R_4$ in the different amide side chains are different, n is different or the optionally double bond in the amide is present or absent.

11. The polyelectrolyte multilayer of claim 10, wherein the two different amide side chains are stereoisomers.

12. The polyelectrolyte multilayer of claim 5, wherein the anionic polymer has the formula:

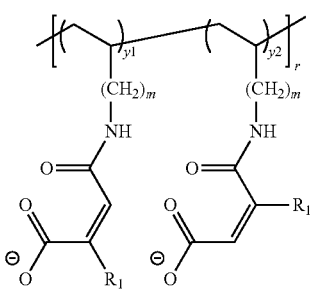

where r is an integer ranging from 5 to 100,000, m is an integer ranging from 1 to 10, y1 and y2 are each integers representing the mole percent of the indicated side chains compared to the total of y1+y2 in the polymer and $R_1$ is selected from optionally substituted alkyl, alkenyl, alkynyl, aryl, heteroaryl, carbocyclic and heterocyclic where optional substituents include one or more halogen, hydroxyl, alkyl, alkenyl, alkynyl, aryl, heteroaryl, carbocyclic or heterocyclic groups, —CN, alkoxyl, —COOH (or —COO⁻), —COOR, or —CON(R')$_2$, where R is alkyl, alkenyl, alkynyl, aryl, heteroaryl, carbocyclic or heterocyclic and each R' is hydrogen or R.

13. The polyelectrolyte multilayer of claim 5, wherein the anionic polymer is a copolymer.

14. The polyelectrolyte multilayer of claim 5 wherein the anionic polymer is a block copolymer wherein at least one block comprises the anionic polymer.

15. The polyelectrolyte multilayer of claim 5 wherein the anionic polymer has formula:

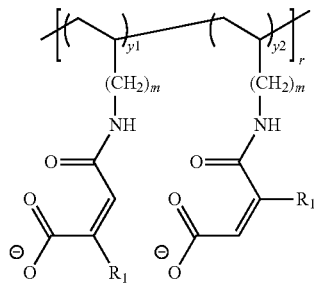

where r is an integer ranging from 5 to 100,000, m is 1-6, $y^1$ and $y^2$ are numbers representing the mole percent of the indicated side group where $y^1+y^2$ is 1; and $R_1$ is an optionally substituted C1-C6 alkyl group.

16. The polyelectrolyte multilayer of claim 15, wherein in the anionic polymer $y^1$ ranges from 0.1 to 0.9.

17. The polyelectrolyte multilayer of claim 5, wherein the anionic polymer has formula:

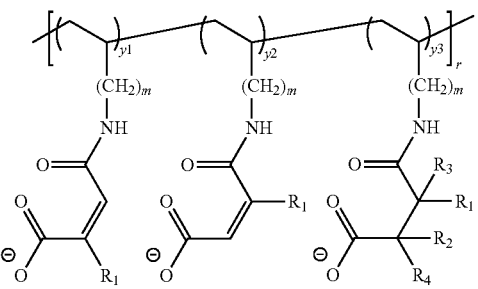

where r is an integer ranging from 5 to 100,000, m is 1-6, $y^1$, $y^2$ and $y^3$ are numbers representing the mole percent of the indicated side group where $y^1+y^2+y^3$ is 1; and $R_1$ is an optionally substituted C1-C6 alkyl group.

18. The polyelectrolyte multilayer of claim 17, wherein in the anionic polymer $y^3$ ranges from 0.01 to 0.90 or $y^3$ ranges from 0.25 to 0.50.

19. A method for controlled delivery of a neutral, zwitterionic, anionic or cationic agent to a selected environment which comprises the steps of:

forming a polyelectrolyte multilayer of claim 5 comprising one or more cations, an anionic polymer and a neutral, zwitterionic, anionic, or cationic agent, where the polyelectrolyte multilayer is in contact with the selected environment; and selectively removing one or more functional groups from the anionic polymer, thereby decreasing the anionic charge of the polymer, disrupting at least one layer of the multilayer and releasing the one or more cations and the neutral, zwitterionic, anionic, or cationic agent into the selected environment.

20. The method of claim 19 wherein the agent is a cationic agent.

21. The polyelectrolyte multilayer of claim 5 wherein the anionic polymer has formula:
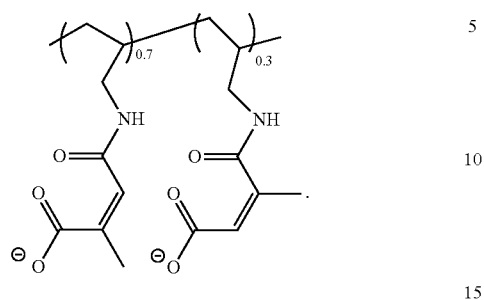
* * * * *